United States Patent [19]

Bright

[11] Patent Number: 5,668,145

[45] Date of Patent: Sep. 16, 1997

[54] AMINO-SUBSTITUTED PYRAZOLES HAVING CRF ANTAGONISTIC ACTIVITY

[75] Inventor: Gene Michael Bright, Groton, Conn.

[73] Assignee: Pfizer Inc., New York, N.Y.

[21] Appl. No.: 448,534

[22] PCT Filed: Nov. 12, 1993

[86] PCT No.: PCT/US93/10716

§ 371 Date: Jun. 14, 1995

§ 102(e) Date: Jun. 14, 1995

[87] PCT Pub. No.: WO94/13644

PCT Pub. Date: Jun. 23, 1994

[51] Int. Cl.⁶ .............. C07D 403/06; C07D 401/06; A61K 31/47; A61K 31/415

[52] U.S. Cl. .............. 514/307; 514/311; 514/314; 514/406; 514/407; 546/148; 546/167; 548/364.1; 548/365.1; 548/367.7; 548/371.4; 548/374.1

[58] Field of Search ............... 546/148, 167; 548/364.1, 365.1, 367.7, 371.4, 374.1; 514/307, 311, 314, 406, 407

[56] References Cited

U.S. PATENT DOCUMENTS 4,605,642  8/1986  Rivier et al. .......................... 514/12
5,063,245  11/1991  Abren et al. .......................... 514/404

OTHER PUBLICATIONS

Sandstrom, Antiviral Therapy in Aids, vol. 34, 1987, pp. 373–390.

M. J. Owens et al., Pharm. Rev., 43(4), 425–473 (1991).

L. K. Altman, "At AIDS Meeting, Experts Find An Uneasy Mix of Hope and Fear," The N.Y. Times, Jul. 9, 1996.

"A Solution for AIDS?", The Economist, Jun. 29, 1996.

M. Waldholz, "Precious Pills," The Wall Street Journal, Jul. 3, 1996.

D. E. Grigoriadis et al., Peptides 10, 179–188 (1989).

E. B. DeSouza, j. Neuroscience 7(1), 88–100 (1987).

M. J. Owens et al., Pharm. Rev. 43(4), 425–473 (1991).

Primary Examiner—Zinna Northington Davis
Attorney, Agent, or Firm—Peter C. Richardson; Paul H. Ginsburg; Bryan C. Zielinski

[57] ABSTRACT

The invention relates to compounds of the formula I

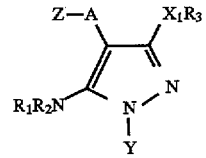

and to pharmaceutically acceptable salts thereof, wherein Z, A, Y, $X_1$, $R_1$, $R_2$, and $R_3$ are as defined herein. The invention further relates to pharmaceutical compositions containing, and to methods of using, the compounds of formula I in the treatment of those disorders that can be treated with compounds having corticotropin-releasing factor antagonistic activity. Such disorders include various stress-related conditions, such as anxiety.

21 Claims, No Drawings

5,668,145

AMINO-SUBSTITUTED PYRAZOLES HAVING CRF ANTAGONISTIC ACTIVITY

This is a national stage application, filed pursuant to 35 U.S.C. §371, of PCT international application number PCT/US93/10716, filed Nov. 12, 1993.

This invention relates to substituted pyrazoles, pharmaceutical compositions containing them, and their use in the treatment of stress-related and other diseases. The compounds have corticotropin-releasing factor (CRF) antagonist activity.

CRF antagonists are mentioned in U.S. Pat. Nos. 4,605,642 and 5,063,245 referring to peptides and pyrazolinones, respectively. The importance of CRF antagonists is set out in the literature, e.g. as discussed in U.S. Pat. No. 5,063,245, which is incorporated herein by reference. A recent outline of the different activities possessed by CRF antagonists is found in M. J. Owens et al., Pharm. Rev., Vol. 43, pages 425 to 473 (1991), also incorporated herein by reference. Based on the research described in these two and other references, CRF antagonists are considered effective in the treatment of a wide range of diseases including stress-related illnesses, such as stress-induced depression, anxiety, and headache; abdominal bowel syndrome, inflammatory diseases; immune suppression; human immunodeficiency virus (HIV) infections; Alzheimer's disease; gastrointestinal diseases; anorexia nervosa; hemorrhagic stress; drug and alcohol withdrawal symptoms; drug addiction, and fertility problems.

The present invention relates to a compound of the formula

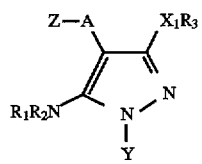

and the pharmaceutically acceptable acid addition salts thereof,
wherein
A is $CH_2$;
$X_1$ is a covalent bond, $CH_2$, O, S, or NR, wherein R is hydrogen, linear $C_1-C_6$ alkyl, or branched $C_3-C_8$ alkyl;
$R_1$, $R_2$ and $R_3$ are each independently linear $C_1-C_6$ alkyl, branched $C_3-C_8$ alkyl, $C_3-C_8$ alkenyl wherein the double bond is not adjacent to the N or $X_1$ when $X_1$ is oxygen or sulfur, or $C_3-C_7$ cycloalkyl $(CH_2)_n$ wherein n is 0, 1, 2, 3 or 4; or $R_1$ and $R_2$ when taken together with the nitrogen form a saturated four, five or six membered ring optionally condensed with benzo; and $R_3$ may also be $(CH_2)_q Q_1 R_{19}$ wherein q is 0, 1 or 2, $Q_1$ is O, S, NH, $N(C_1-C_6$ alkyl) or a covalent bond when $X_1$ is not a covalent bond, and $R_{19}$ is hydrogen, linear $C_1-C_6$ alkyl, branched $C_3-C_8$, $C_3-C_8$ alkenyl, or $C_3-C_6$ cycloalkyl $(CH_2)_n$ wherein n is 0 to 4;
Y is phenyl, thienyl, benzothienyl, pyridyl, quinolyl, pyrazinolyl, pyrimidyl, imidazolyl, benzimidazolyl, furanyl, benzofuranyl, thiazolyl, benzothiazolyl, isothiazolyl, benzisothiazolyl, isoxazolyl, benzisoxazolyl, triazolyl, pyrazolyl, pyrrolyl, indolyl, azaindolyl, oxazolyl, benzoxazolyl, pyrrolidinyl, thiazolidinyl, morpholinyl, or piperidinyl, each of which may be substituted by one to three of any one of fluoro, chloro, bromo, or methyl, or one of trifluoromethyl; with the proviso that Y is not unsubstituted phenyl; and Z is (a)

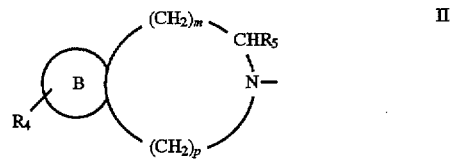

wherein the B ring is phenyl, naphthyl, pyridyl, pyrimidinyl, pyrazinyl, pyridazinyl, triazilyl, pyrrolyl, pyrazolyl, imidazolyl, triazolyl, thienyl, or indolyl, each of which may be substituted by methyl methoxy, fluoro, chloro, bromo or iodo; or a saturated 5- or 6-membered carbocyclic ring or a partially unsaturated ring having one or two double bonds;
$R_4$ is hydrogen, $C_1-C_6$ alkyl, $C_1-C_6$ alkoxy, hydroxy, fluoro, chloro, bromo, iodo, or trifluoromethyl;
$R_5$ is hydrogen, linear $C_1-C_6$ alkyl, branched $C_3-C_8$ alkyl, $C_3-C_8$ alkenyl, or $(CH_2)_o-X_2-(CH_2)_r-Q_2-R_6$;
$R_6$ s is hydrogen, linear $C_1-C_6$ alkyl, branched $C_3-C_8$ alkyl, or $C_3-C_8$ alkenyl;
$X_2$ and $Q_2$ are each independently O, S, NH, $N(C_1-C_6$ alkyl), or one of $X_2$ and $Q_2$ may be a covalent bond;
m is 0 or 1;
o is 1 or 2;
p is 1 or 2; and
r is 0, 1, or 2;

(b)

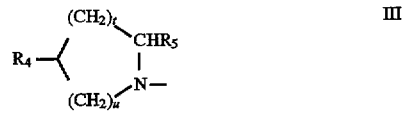

wherein $R_4$ and $R_5$ are as defined above, and t and u are each independently 1 or 2;

(c) $-NR_7R_8$ wherein $R_7$ and $R_8$ are each independently hydrogen, $C_1-C_6$ linear alkyl, branched $C_3-C_8$ alkyl, $C_3-C_8$ alkenyl, $(CH_2)_v CH_2OH$, $(CH_2)_v NR_9 R_{10}$, wherein v is 0 to 3, and $R_9$ and $R_{10}$ are each independently hydrogen, or linear $C_1-C_6$ alkyl; $C_1-C_{12}$ cycloalkyl, $(C_3-C_{12}$ cycloalkyl) $(CH_2)_n$, $(C_6-C_{10}$ bicycloalkyl) $(CH_2)_n$, wherein n is 0 to 4, benzofused $C_3-C_6$ cycloalkyl, $C_1-C_6$ hydroxyalkyl, phenyl, phenyl $(C_1-C_3$ alkylene), each of which may be substituted by one or two of hydroxy, fluoro, chloro, bromo, $C_1-C_5$ alkyl, or $C_1-C_5$ alkoxy; or $R_7$ and $R_8$ may be taken together with the nitrogen to form a saturated or partially unsaturated 5- to 7-membered ring which may contain one of O, S, NH or $N(C_1-C_6$ alkyl) and which may be substituted by $C_1-C_6$ alkyl, hydroxy or phenyl wherein any double bond(s) are not adjacent to any heteroatoms;

(d)

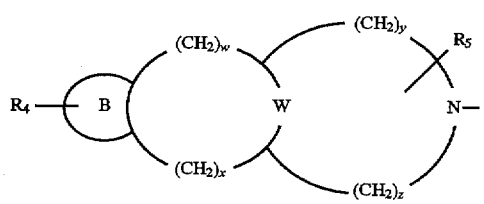

wherein B, $R_4$ and $R_5$ are as defined above, w, x, y and z are each independently 1 or 2, and W is $(CH_2)_q$ wherein q is as defined above, $N(C_1-C_6$ alkyl), or oxygen;

(e)

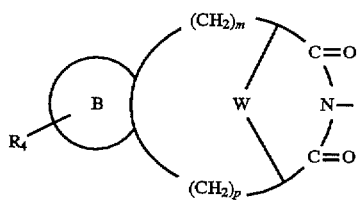

wherein B, $R_4$, m and p are as defined above;

(f)

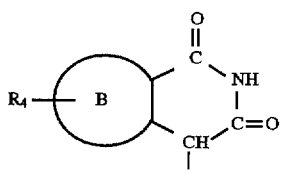

wherein B and $R_4$ are as defined above;

(g) $O(CH_2)_vR_{11}$ wherein v is 0 to 3 and $R_{11}$ is linear $C_1-C_6$ alkyl, branched $C_3-C_8$ alkyl, phenyl, naphthyl, 1,2,3,4-tetrahydronaphthyl, thienyl, benzothienyl, pyridyl, quinolyl, pyrazinolyl, pyrimidyl, imidazolyl, benzimidazolyl, furanyl, benzofuranyl, thiazolyl, benzothiazolyl, isothiazolyl, benzisothiazolyl, isoxazolyl, benzisoxazolyl, triazolyl, pyrazolyl, pyrrolyl, indolyl, azaindolyl, oxazolyl, benzoxazolyl, pyrrolidinyl, thiazolidinyl, morpholinyl, piperidinyl, or thienyl, each of which may be substituted by one or two of any one of fluoro, chloro, bromo, methyl, or trifluoromethyl;

(h)

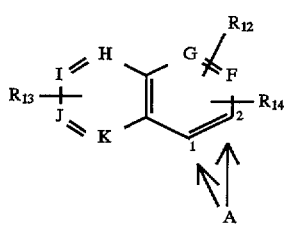

wherein A is defined above and is linked to position 1 or 2 while $R_{14}$ is attached to position 2 or 1, respectively; F, G, H, I, J and K are independently C or N, provided that not more than three of H, I, J and K are N with not more than two adjacent nitrogens; $R_{12}$ and $R_{13}$ each independently are hydrogen, linear $C_1-C_6$ alkyl, branched $C_3-C_8$ alkyl, $C_3-C_8$ alkenyl, fluoro, chloro, bromo, trifluoromethyl, hydroxy, thiol, $C_1-C_{12}$ alkoxy, $C_1-C_{12}$ thioalkanyl, or $C_3-C_{12}$ alkenoxy or $C_3-C_{12}$ thioalkenyl wherein the double bond is not adjacent to the oxygen or sulfur, and $R_{14}$ is hydroxy, $C_1-C_{12}$ alkoxy, $C_3-C_{12}$ alkenoxy wherein the double bond is not adjacent to the oxygen, or $—X_2—(CH_2)_rQ_2R_6$ wherein $X_2$, r, $Q_2$ and $R_6$ are as defined above in paragraph (a) except that Q is not sulfur, or $R_{14}$ is $NR_{15}R_{16}$ wherein $R_{15}$ and $R_{16}$ are each independently hydrogen, linear $C_1-C_6$ alkyl, branched $C_3-C_8$ alkyl, $C_3-C_8$ alkenyl wherein the double bond is not adjacent to the nitrogen, or $C_3-C_7$ cycloalkyl-$(CH_2)_n$ wherein n is as defined above, or $R_{15}$ and $R_{16}$ together with the nitrogen form a saturated five or six membered ring optionally condensed with benzo; or (i)

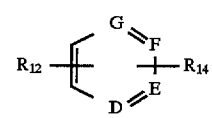

wherein D, E, F and G are independently C or N, provided that not more than two of D, E, F and G are N, and $R_{12}$ and $R_{14}$ are as defined in paragraph (h), A, defined above, is linked to a carbon in formula XV, and $R_{14}$ is linked to a carbon located adjacent to the carbon to which A is linked.

More specific compounds of formula I of the invention include those wherein Y is phenyl substituted by three substituents one each at positions 2, 4 and 6, e.g. 2,4,6-trichlorophenyl, 2,6-dichloro-4-trifluoromethylphenyl, or 2,6-dichloro-4-fluorophenyl. Other more specific compounds of formula I include those wherein $XR_3$ is ethyl or methylthio, those wherein $R_1$ and $R_3$ are each methyl, and those wherein Z is $NR_7R_8$ and $R_7$ is phenyl or phenyl substituted by one of fluoro, chloro, nitro, methyl or methoxy and $R_8$ is as defined above, preferably, $(CH_2)_3OH$, $CH_2CH_2OH$ or methyl.

Preferred compounds of formula I are those wherein Z is 1,2,3,4-tetrahydroisoquinolin-2-yl substituted by $R_5$ which is $—(CH_2)_o—X_2—(CH_2)_r—Q_2—R_6$, more specifically $R_5$ is $—(CH_2)_kOH$ wherein k is an integer of 1 to 4, or $—CH_2OCH_2CH_2OR_6$. Other preferred compounds of formula I are those wherein Z is 1,2,3,4-tetrahydroquinolin-2-yl wherein $R_5$ is substituted at position 3, and the absolute configuration at the 3 position is either S or R or R,S.

Preferred compounds of the formula I include those wherein Z is as defined in above subparagraph (h); and those wherein Z is as defined in (h), A is linked to position 1, F, G, H, I, J and K are each carbon, and $R_{14}$ is methoxy, ethoxy, isopropoxy, or cyclopropylmethoxy at position 2.

Other preferred compounds of formula I are those wherein Z is as defined in above subparagraph (h), A is linked to position 1, K is nitrogen, F, G, H, I, and J are each carbon, and $R_{14}$ is $—X_2—(CH_2)_rQ_2R_6$ at position 2; those wherein Z is as defined in (h), A is linked to position 1, K is nitrogen, F, G, H, I, and J are each carbon, and $R_{14}$ is methoxy, ethoxy, isopropoxy, or cyclopropylmethoxy at position 2; and those wherein Z is as defined in (h), A is at position 1, and $R_{14}$ is ethoxy, isopropoxy or cyclopropylmethoxy at position 2. In these preferred compounds of formula I wherein Z is as defined in (h), $R_{12}$ and $R_{13}$ are preferably hydrogen.

Other preferred compounds of formula I are those wherein Z is as defined in subparagraph (a), B is phenyl, p and m are each 1, and $R_5$ is $CH_2OCH_3$.

Preferred compounds of formula I include those wherein Z is

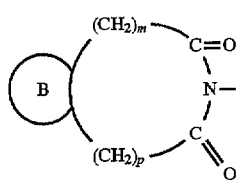

wherein B is phenyl, m is 0, and p is 1.

Specific most preferred compounds of the invention include:

2-{1-[1-(2,6-dichloro-4-trifluoromethylphenyl)-5-dimethylamino-3-ethyl-1H-pyrazol-4-ylmethyl]-napthalen-2-yloxy}-ethanol;

enantiomeric [4-(3-methoxymethyl-3,4-dihydro-1H-isoquinolin-2-ylmethyl)-5-methylsulfanyl-2-(2,4,6-trichlorophenyl)-2H-pyrazol-3-yl]-dimethylamine derived from (+)-3-hydroxymethyl-1,2,3,4-tetrahydroisoquinoline;

enantiomeric [2-(2,6-dichloro-4-trifluoromethylphenyl)-4-(3-ethoxymethyl-3,4-dihydro-1H-isoquinolin-2-ylmethyl)-5-ethyl-2H-pyrazol-3-yl]-dimethylamine derived from (+)-3-hydroxymethyl-1,2,3,4-tetrahydroisoquinoline;

[2-(2,6-dichloro-4-trifluoromethylphenyl)-5-ethyl-4-(7-methoxyquinolin-8-ylmethyl)-2H-pyrazol-3-yl]-dimethylamine;

[2-(2,6-dichloro-4-trifluoromethylphenyl)-4-(2-ethoxy-napthalen-1-ylmethyl)-5-ethyl-2H-pyrazol-3-yl]-dimethylamine;

[4-(2-ethoxynapthalen-1-ylmethyl)-5-ethyl-2-(2,4,6-trichlorophenyl)-2H-pyrazol-3-yl]-dimethylamine;

[4-(7-methoxyquinolin-8-ylmethyl)-5-methylsulfanyl-2-(2,4,6-trichlorophenyl)-2H-pyrazol-3-yl]-dimethylamine;

2-{1-[5-dimethylamino-3-methylsulfanyl-1-(2,4,6-trichlorophenyl)-1H-pyrazol-4-ylmethyl]-napthalen-2-yloxy}-ethanol;

enantiomeric [2-(2,6-dichloro-4-trifluoromethylphenyl)-5-ethyl-4-(3-methoxymethyl-3,4-dihydro-1H-isoquinolin-2-ylmethyl)-2H-pyrazol-3-yl]-dimethylamine derived from (+)-3-hydroxymethyl-1,2,3,4-tetrahydroisoquiniline;

[4-(2-cyclopropylmethoxynapthalen-1-ylmethyl)-5-methylsulfanyl-2-(2,4,6-trichlorophenyl)-2H-pyrazol-3-yl]-dimethylamine;

2-{[5-dimethylamino-3-ethyl-1-(2,4,6-trimethylphenyl)-1H-pyrazol-4-ylmethyl]-naphthalen-2-yloxy}-ethanol;

2-{1-[5-dimethylamino-3-methylsulfanyl-1-(2,4,6-trimethylphenyl)-1H-pyrazol-4-ylmethyl]-naphthalen-2-yloxy}-ethanol;

[2-(2,6-dichloro-4-trifluoromethylphenyl)-5-methoxymethyl-4-(2-methoxy-naphthalen-1-ylmethyl)-2H-pyrazol-3-yl]-dimethylamine;

2-{1-[5-dimethylamino-3-ethyl-1-(2,4,6-trichlorophenyl)-1H-pyrazol-4-ylmethyl]-napthalen-2-yloxy}-ethanol;

[5-ethyl-4-(2-methoxy-naphthalen-1-ylmethyl)-2-(2,4,6-trimethylphenyl)-2H-pyrazol-3-yl]-dimethylamine;

2-{2-[1-(2,6-dichloro-4-trifluoromethylphenyl)-5-dimethylamino-3-ethyl-1H-pyrazol-4-ylmethyl]-1,2,3,4-tetrahydroisoquinolin-3-ylmethoxy}-ethanol;

[4-(3-methoxymethyl-3,4-dihydro-1H-isoquinolin-2-ylmethyl)-5-methylsulfanyl-2-(2,4,6-trimethylphenyl)-2H-pyrazol-3-yl]-dimethylamine; and 2-{2-[5-dimethylamino-3-ethyl-1-(2,4,6-trichlorophenyl)-1H-pyrazol-4-ylmethyl]-1,2,3,4-tetrahydroisoquinolin-3-ylmethoxy}-ethanol.

The invention also relates to a compound of the formula 1A (not shown) and the pharmaceutically acceptable acid addition salts thereof. The compounds of the formula 1A are identical to those of the formula I except that A is CH($C_1$–$C_6$ alkyl), C($C_1$–$C_6$ alkyl)$_2$, C($C_1$–$C_6$ alkyl)($C_3$–$C_8$ alkenyl), CH(CH$_2$)$_n$($C_3$–$C_8$ alkenyl) wherein n is 0 to 4 or C($C_3$–$C_8$ alkenyl)$_2$.

The invention includes a pharmaceutical composition for the treatment of illnesses induced or facilitated by corticotropin releasing factor which comprises a compound of the formula I or IA as defined above in an amount effective in the treatment of said illnesses, and a pharmaceutically acceptable carrier, and a composition for the treatment of inflammatory disorders, stress and anxiety related disorders including stress-induced depression and headache, abdominal bowel syndrome, immune suppression, HIV infections, Alzheimer's disease, gastrointestinal diseases, anorexia nervosa, hemorrhagic stress, drug and alcohol withdrawal symtoms, drug addiction, and fertility problems, which comprises a compound of the formula I or IA as defined above in an amount effective in the treatment of said disorders, and a pharmaceutically acceptable carder. Preferred and more specific compositions of the invention are those containing preferred and more specific compounds of formula I as described above.

The invention further relates to a method for the treatment of illnesses induced or facilitated by coritcotropin releasing factor by administering to a subject in need of such treatment a compound of formula I or IA as defined above, and a method for the treatment of stress and anxiety related disorders including stress-induced depression and headache, abdominal bowel syndrome, inflammatory disorders, immune suppression HIV infections Alzheimer's disease, gastrointestinal diseases, anorexia nervosa, hemorrhagic stress, drug and alcohol withdrawal symtoms, drug addiction, and fertility problems, particularly depression, by administering to a subject in need of such treatment a compound of formula I or IA as defined above. Preferred and more specific methods of the invention are those administering preferred and more specific compound of the formula I as described above.

The invention also relates to an intermediate compound of the formula

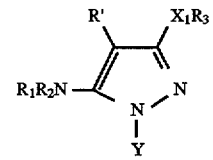

wherein R' is CH$_2$OH or C(O)O($C_1$–$C_3$ alkyl), $R_1$, $R_2$ and $R_3$ are each independently linear $C_1$–$C_6$ alkyl, branched $C_3$–$C_8$ alkyl, $C_3$–$C_8$ alkenyl wherein the double bond is not adjacent to the N or $X_1$ when $X_1$ is oxygen or sulfur, $C_3$–$C_7$ cycloalkyl (CH$_2$)$_n$ wherein n is 0, 1, 2, 3 or 4; or $R_1$ and $R_2$ when taken together with the nitrogen form a saturated four, five or six membered ring optionally condensed with benzo;

$X_1$ is a covalent bond, CH$_2$NR wherein R is hydrogen or linear $C_1$–$C_6$ alkyl, O, or S; and Y is phenyl, thienyl, benzothienyl, pyridyl, quinolyl, pyrazinolyl, pyrimidyl, imidazolyl, benzimidazolyl, furanyl, benzofuranyl, thiazolyl, benzothiazolyl, isothiazolyl, benzisothiazolyl, isoxazolyl, benzisoxazolyl, triazolyl, pyrazolyl, pyrrolyl, indolyl, azaindolyl, oxazolyl, benzoxazolyl, pyrrolidinyl, thiazolidinyl, morpholinyl, or piperidinyl, each of which may be substituted by one to three of any one of fluoro, chloro, bromo, or methyl, or one of trifluoromethyl; with the proviso that Y is not unsubstituted phenyl.

Whenever reference herein is made to groups $(CH_2)_qQ_1R_{19}$ and $(CH_2)_o—X_2—CH_2)_r—Q_2—R_6$, then $X_1$ and $Q_1$, and $X_2$ and $Q_2$, respectively, are not both a heteroatom when q or r, respectively, is 1.

Whenever Y or $R_{11}$ is a heterocyclic group, the attachment of the group is through a carbon atom.

The compounds of formula I may be prepared by reaction of a compound of the formula

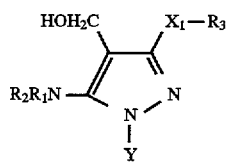

VIII with a sulfonyl chloride such as methylsulfonylchloride, in a solvent such as methylene chloride or toluene, at temperatures of about −10° to about 30° C., followed by reaction with a compound of the formula ZH or ZMetal wherein Z is as defined above and Metal is an alkali metal such as sodium, lithium or potassium. The reaction with ZH proceeds generally in the presence of a solvent such as methylene chloride or toluene at temperatures of about 50° to about 100° C. in the presence of a strong base such as an alkali metal hydride, e.g. sodium hydride, lithium hydride or potassium hydride, except when ZH is a sufficiently strong base itself, in which case a stoichiometric excess of ZH may be used or a stoichiometric mount of ZH in the presence of a suitably strong base such as a trialkylamine, e.g. triethylamine. The reaction with ZMetal proceeds in solvents such as N,N-dimethylformamide at temperatures in the range of about 50° to about 100° C.

The compounds of formula VIII may be prepared by reacting a compound of the formula

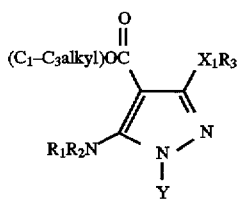

IX wherein $X_1$, Y, $R_1$, $R_2$ and $R_3$ are as defined with reference to formula I, except that $R_1$ and $R_2$ are not hydrogen, with a reducing agent which is compatible with the chemical substituents on the aminopyrazole ring, such as diisobutylaluminum hydride in a reaction inert solvent such as tetrahydrofuran or ether, at temperatures of about −5° to 30° C.

The compounds of the formula IX may be prepared from the corresponding compounds wherein $R_1$, and $R_2$ are hydrogen (formula X, not shown) by reacting first with an alkali metal hydride such as sodium hydride and then with alkylating agents $R_1$Hal and $R_2$Hal wherein Hal is chloro or bromo and $R_1$ and $R_2$ are as defined with reference to formula I except hydrogen, in a solvent such as tetrahydrofuran at temperatures of about 5° to 80° C.

The compounds of the formula X may be prepared by reacting a 2-cyano-acrylic acid ester of the formulae

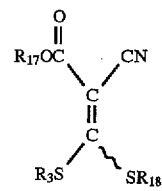

XI to make a compound of the formula I wherein $X_1$ is S,

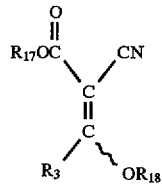

XII to make a compound of formula I wherein $X_1$ is a covalent bond,

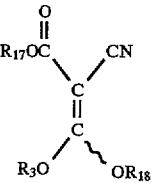

XIII to make a compound of formula I wherein $X_1$ is O, or

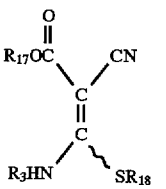

XIV to make a compound of formula I wherein $X_1$ is NR and R is hydrogen, wherein $R_{17}$ is $C_1$–$C_3$ alkyl and $R_{18}$ is $C_1$–$C_2$ alkyl, with a hydrazine of the formula $NH_2NHY$ wherein Y is as defined with reference to formula I. The reaction is carried out in a solvent, such as a $C_1$–$C_8$ alcohol, at about 50° to 150° C., conveniently the reflux temperature of the reaction mixture. The wavy line ~~ in some of the formulae herein indicates that either isomer of this compound is included, in accordance with accepted convention for indicating stereoisomers.

The intermediates of formula IX obtained by the above reaction from the compound of formula XIV have the formula

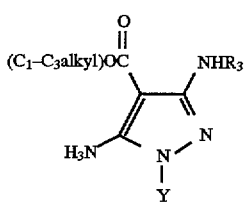

IXA

They may be trialkylated by using at least three equivalents of alkali metal hydride and $R_2$Hal wherein Hal is chloro or bromo, in the manner described above for conversion of the compounds of formula X to the compounds of formula IX, to obtain the compounds of formula I wherein $R_1$, $R_2$ and R are as defined above with reference to formula I other than hydrogen.

The above intermediates of the formula IXA may be reacted with a compound providing an N-protecting group to replace the hydrogen in the NHR₃ group followed by alkylation with R₂Hal or R₃Hal and removal of the N-protecting group to provide the compounds of the formula I wherein X₁ is NRR₃ wherein R is hydrogen, and R₂ and R₃ are as defined above with reference to formula I other than hydrogen.

Reaction of the compounds of the formula

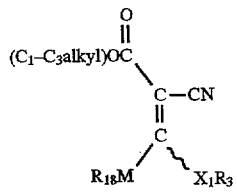

XV wherein M is X₁ is S and R₃ is R₁₈ is C₁–C₆ alkyl with mines such as RNH₂ or RR₃NH in an appropriate solvent such as ethanol at temperatures of about 0° to about 100° C. results in compounds of the formula XV in which R₁₈-M and X₁-R₃ are each RNH or NRR₃, wherein R is as defined with reference to formula I and R₃ is linear alkyl, branched C₃–C₈ alkyl, or C₃–C₈ alkenyl wherein the double bond is not adjacent to the nitrogen.

The compounds of formula I wherein Z is as defined above in paragraphs (a), (h) or (i) wherein R₅ or R₁₄ is X₂(CH₂)ᵣQ₂R₆, wherein Q₂ is oxygen, and X₂, r, and R₆ as previously defined except that R₆ is not hydrogen, may be prepared by alkylation of the corresponding compound wherein R₅ or R₁₄ are (CH₂)ₒ—X₂—(CH₂)₂—Q₂—R₆ and —X₂—(CH₂)ᵣQ₂R₆, respectively, wherein R₆ is hydrogen and Q₂ is oxygen. In these case wherein R₅ and R₁₄ have a terminal hydroxy group, the hydroxy is first reacted with a strong base such as an alkali metal hydride, e.g. lithium, sodium or potassium hydride, in a solvent such as dimethylformamide at about 50° to 100° C.

The resulting alkali metal alkoxide is then reacted with an alkyl or aryl sulfonyl ester of the formula HO(CH₂)ᵣQ₂R₆ wherein R₆ is as defined in paragraph (a) except hydrogen. This reaction is carded out in the presence of a solvent such as methylene chloride or toluene at about 50° to 100° C. The above sulfonyl esters may be prepared by the same method as described above for the activation of the compound of formula IX.

The above alkali metal hydride may be replaced by other strong bases including organometallic bases such as n-butyl lithium or amine anion bases such as lithium diisopropylamide. In such case, the metal alkoxide formation reaction may be carried out in tetrahydrofuran at temperatures of about −5° to about 65° C.

The above alkylation may also be used to prepare compounds of the formula I wherein X₁ is oxygen and R₃ is (CH₂)qQ₁R₁₉ wherein q, Q₁ and R₁₉ are as defined above with reference to formula I except that R₁₉ is not hydroxy, from the corresponding compounds wherein X₁R₃ is hydroxy.

The compounds of formula IA wherein A is CH(C₁–C₆ alkyl), or CH(CH₂)ₙ(C₃–C₈ alkenyl) wherein n is 0 to 4 (having formula IB, not shown) may be prepared from the compounds of formula IX by reaction with a Grignard reagent of the formula R₁₉MgHal wherein R₁₉ is C₁–C₆ alkyl, or (CH₂)ₙ(C₃–C₈ alkenyl) wherein n is 0 to 4, in a conventional manner, e.g. in diethyl ether or tetrahydrofuran solvent at about −78° to 50° C., to form a ketone of the formula

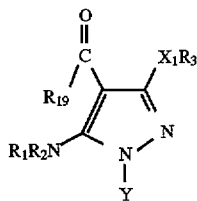

XVI

The ketone XVI may be converted to the corresponding enamine by reaction with a compound of the formula ZH wherein Z is (a) to (d) as defined above under standard acid catalyzed dehydrogenation conditions. The enamine may be converted into the compounds of formula IA wherein A is CHR₁₉ by hydrogenation with hydrogen under pressure in the presence of a noble metal catalyst or reduction with a hydride such as sodium or lithium cyanoborohydride in diethylether or tetrahydrofuran (THF).

Alternatively, the compounds of formula IB may be prepared from compounds IX by reaction with ZH wherein Z is (a) to (d) as defined above in the presence of a hydride reducing agent such as sodium or lithium cyanoborohydride.

The compounds of formula IA wherein A is C(C₁–C₆ alkyl)₂, C(C₁–C₆ alkyl)(C₃–C₈ alkenyl) or C(C₃–C₈ alkenyl)₂ may be prepared from the compound of formula IX by reaction with concentrated hydrochloric add under reflux to form a compound of the formula

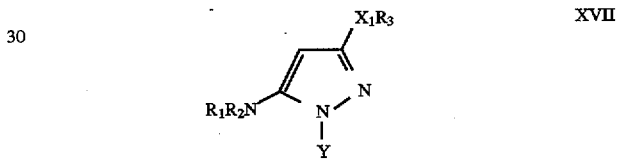

XVII

The compound XVII may be brominated, e.g. with pyridinium bromide in THF, to form the corresponding 4-bromide of formula XVIII (not shown) which may be 4-metalated in situ, such as with t-butyl lithium in diethyl ether at −78° C., and then treated in situ with an iminium compound of the formula

wherein R₁₉ is as defined above, R₂₀ is R₁₉, Z is (a) to (d) as defined above, and X is halogen.

The compounds of formula IA wherein A is CHR₁₉ wherein R₁₉ is as defined above, Z is (h) or (i) as defined above and R¹⁴ does not have acidic hydrogens, such as hydroxyls, may be prepared from compounds of the formula I wherein Z is (h) or (i) and the other substituents are as defined above with reference to formula I by treatment with a strong base such as t-butyl lithium in ether or THF and subsequent alkylation in the same solvent with a halide of the formula R₁₉X wherein R₁₉ and X are as defined above.

When the compounds of the invention contain a chiral center, it is understood that the invention includes the racemic mixture and the individual enantiomers of such compounds. For instance, the compounds of the invention wherein Z is 1,2,3,4-tetrahydroisoquinolinyl have a chiral center when Z is substituted at position 3 by R₅, wherein R₅ is as defined with reference to formula I except hydrogen, as follows:

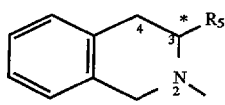

wherein the chiral center is indicated by an asterisk.

Preferred compounds of the invention of formula I or IA include those derived from the dextrorotatory (+) enantiomer of the intermediate compound ZH of the formula:

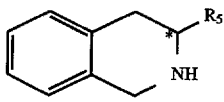

wherein $R_5$ is hydroxymethyl or $(C_1-C_6$ alkoxy)methyl.

The acid addition salts are prepared in a conventional manner by treating a solution or suspension of the free base of formula I or IA with one chemical equivalent of a pharmaceutically acceptable acid. Conventional concentration or crystallization techniques are employed in isolating the salts. Illustrative of suitable acids are acetic, lactic, succinic, maleic, tartaric, citric, gluconic, ascorbic, benzoic, cinnamic, fumaric, sulfuric, phosphoric, hydrochloric, hydrobromic, hydroiodic, sulfamic, sulfonic acids such as methanesulfonic, benzenesulfonic, p-toluenesulfonic, and related acids.

The compound of the invention may be administered alone or in combination with pharmaceutically acceptable carders, in either single or multiple doses. Suitable pharmaceutical carriers include inert solid diluents or fillers, sterile aqueous solution and various organic solvents. The pharmaceutical compositions formed by combining the novel compounds of formula I or IA and the pharmaceutically acceptable carriers are then readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions of the novel compound of formula I in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. The sterile aqueous media employed are all readily available by standard techniques known to those skilled in the art.

Additionally, it is possible to administer the compounds of the present invention topically when treating inflammatory conditions of the skin and this may be done by way of creams, jellies, gels, pastes, and ointments, in accordance with standard pharmaceutical practice.

The effective dosage for the compound of formula I or IA depends on the intended route of administration and other factors such as age and weight of the patient, as generally known to a physician. The dosage also depends on the illness to be treated, although the daily dosage for the illnesses to be treated according to the invention, as listed above, will generally range from about 0.1 to about 50 mg/kg of the body weight of the patient to be treated. More specifically, for treatment of inflammatory diseases about 0.1 to about 100 mg/kg will be needed, for Alzheimer's disease about 0.1 to about 50 mg/kg, as well as for stress-induced illnesses, gastrointestinal diseases, anorexia nervosa, hemorrhagic stress, drug and alcohol withdrawal symptoms, and fertility problems.

The methods for testing the compounds of formula I or IA for their CRF antagonist activity are as described in Endocrinology, 116, 1653–1659 (1985) and Peptides, 10, 179–188 (1985) which determine the binding activity of a test compound to a CRF receptor. The binding activity for the compounds of formula I and IA generally ranges from about 0.2 nanomolar to about 10 micromolar.

The following Examples illustrate the invention.

EXAMPLE 1

A. 5-Amino-3-methylsulfanyl-1-(2,4,6-trichlorophenyl)-1H-pyrazole-4-carboxylic acid methyl ester An ethanol (3.5 l) solution of 2-cyano-3,3-bis-methylsulfanyl-acrylic acid methyl ester (454.3 g, 2.23 mol) and 2,4,6-trichlorophenylhydrazine (472.7 g, 2.23 mol) was vigorously refluxed for 1.5 hours. The reaction mixture was allowed to stand overnight at ambient temperature. Water (850 ml) was added, and the resulting mixture was briskly stirred for 30 minutes. The granular precipitate was filtered and washed with a water/ethanol(1:3 in volume)solution (1 l). The air-dried product was further dried under vacuum (45° C.) for 2 days to afford the title compound as a yellow crystalline solid, m.p. 160°–162° C.

B. 5-Dimethylamino-3-methylsulfanyl-1-2,4,6-trichlorophenyl)-1H-pyrazole-4-carboxylic acid methyl ester To a well-stirred and ice-bath-chilled slurry of sodium hydride (232.4 g of 60% sodium hydride mineral oil dispersion, 139.4 g, 5.81 mol of sodium hydride) in anhydrous tetrahydrofuran (4 l), 711.6 g of the compound of Step A (1.94 mol) dissolved in anhydrous tetrahydrofuran was rapidly added dropwise, followed by slow dropwise addition of methyl iodide (1376 g, 9.7 mol). The reaction was then stirred at ambient temperature under nitrogen for 18 hours. The solvent was removed in vacuo. Ethyl acetate (2 l) and water (3 l) were added to dissolve the residue. The separated aqueous phase was extracted twice with 2 l portions of ethyl acetate. The combined organic extracts were washed with brine, dried over anhydrous sodium sulfate and concentrated in vacuo to afford the title compound as an amorphous solid in quantitative yield.

$^{13}$C NMR (CDCl$_3$): 163.0, 156.9, 152.7, 136.0, 135.8, 134.2, 128.8, 51.1, 42.0, 13.4.

C. (5-Dimethylamino-3-methylsulfanyl-1-(2,4,6-trichlorophenyl)-1H-pyrazol-4-yl)-methanol To a well-stirred/ice-bath-chilled solution of the compound of Step B (322 g, 0.816 mol) in anhydrous tetrahydrofuran (4.5 l), diisobutylaluminum hydride (2.863 l of a 1.0M tetrahydrofuran solution, 2.86 mol) was added dropwise over 2 hours. The reaction mixture was then stirred for an additional 40 minutes at 0°–5° C. prior to quenching (with ice-bath cooling) by addition of methanol (400 ml). A 1:1 (in volume) saturated aqueous Rochelle Salts/water solution (4 l), and ethyl acetate (3 l) was added, with good stirring. The organic phase was separated, extracted sequentially with equal volumes of water and brine, and finally, dried with anhydrous magnesium sulfate. Concentration in vacuo afforded a solid residue which crystallized from cyclohexane (3 l) to afford the title compound 132 g as a colorless crystalline solid, m.p. 108°–110° C.

EXAMPLE 2

A. 5-Amino-1-(2,6-dichloro-4-trifluoromethyl-phenyl)-3-methyl-sulfanyl-1H-pyrazole-4-carboxylic acid methyl ester 2-Cyano-3,3-bis-methylsulfanyl-acrylic acid methyl ester (49.8 g, 0.245 mol) and 2,6-dichloro-4-trifluoromethylphenylhydrazine (60.0 g, 0.245 mol) in anhydrous ethanol (390 ml) were combined, and the reaction mixture was vigorously refluxed for 1.5 hours. To the still-warm, well-stirred solution, water (480 ml) was added continuously (dropwise, rapid stream) over 10 minutes. Overnight stirring at ambient temperature afforded a heavy colorless solid precipitate of the title compound, isolated by suction filtration and in vacuo drying (80.7 g).

$^1$H NMR (CDCl$_3$): 2.44 (3H, s), 3.82 (3H, s), 5.18 (2H, s), 7.73 (2H, s).

B. 1-(2,6-Dichloro-4-trifluoromethyl-phenyl)-5-dimethylamino-3-methylsulfanyl-1H-pyrazole-4-carboxylic acid methyl ester To a well-stirred solution of the compound of Step A (35.4 g, 88.45 mmol) and methyl iodide (55.08 ml, 125.53 g, 0.884 mol) in anhydrous tetrahydrofuran (255 ml) chilled to 5° C., sodium hydride (10.62 g of 60% sodium hydride in mineral oil dispersion; 6.37 g, 0.266 mol of sodium hydride) was added portionwise over 10 minutes. The mixture was then vigorously refluxed for 5 hours. Inspection by thin layer chromatography showed complete reaction. The mixture was concentrated in vacuo to a solid which was then dissolved in an ethyl acetate/water mixture (150 ml of each), with the pH adjusted to 9 with sodium carbonate. The organic extract was separated, dried over anhydrous sodium sulfate, and concentrated in vacuo to afford the title compound as a colorless amorphous solid, 41.16 g.

$^1$H NMR (CDCl$_3$): 2.44 (3H, s), 2.72 (6H, s), 3.86 (3H, s), 7.71 (2H, s).

C. [1-(2,6-Dichloro-4-trifluoromethyl-phenyl)-5-dimethyl-amino-3-methylsulfanyl-1H-pyrazol-4-yl-]-methanol To a well-stirred solution of the compound of Step B (6.4 g, 14.9 mmol) in anhydrous tetrahydrofuran (175 ml) maintained at −78° C., diisobutyl aluminum hydride in toluene (49.3 ml of a 1.0M solution, 49.3 mmol was slowly added dropwise over 10 minutes. Thin layer chromatography inspection of an aliquot after 20 minutes of stirring at −78° C. showed incomplete reaction. The reaction mixture was immediately warmed to ambient temperature. Within 20 minutes at ambient temperature, reaction was found to be complete. (In addition to the desired product, a less polar byproduct identified as the corresponding C-4 methyl derivative, is formed). Methanol (162 ml) was added, cautiously at first, to quench the reaction. Warming of the mixture to 35° C. for 15 minutes produced a granular precipitate. The reaction was concentrated in vacuo to a solid, which was extracted with ethyl acetate (150 ml). The solids were separated from the organic extract by filtration. The filtrate was concentrated in vacuo to an oil. Flash chromatography of the entire sample (silica gel, 40 micron mesh; elution with ethyl acetate/hexane, 1:3 in volume) afforded 1.93 g of the title compound as a colorless amorphous foam.

$^1$H NMR (CDCl$_3$): 2.50 (3H, s), 2.70 (6H, s), 4.50 (2H, s), 7.70 (2H, s).

EXAMPLE 3

A. 5-Amino-1-(4-bromo-2,6-dimethyl-phenyl)-3-methyl-sulfanyl-1H-pyrazole-4-carboxylic acid methyl ester In accordance with Example 2A, 4-bromo-2,6-dimethylphenylhydrazine (11.17 g, 55 mmol) was reacted with 2-cyano-3,3-bis-methylsulfanyl-acrylic acid methyl ester (13.8 g, 55 mmol) in 90 ml of ethanol. The title compound was obtained as a light-yellow amorphous solid, 13.0 g.

$^1$H NMR (CDCl$_3$): 2.06 (6H, s), 2.48 (3H, s), 3.86 (3H, s), 4.94 (2H, s), 7.32 (2H, s).

B. 1-(4-Bromo-2,6-dimethyl-phenyl)-5-dimethylamino-3-methylsulfanyl-1H-pyrazole-4-carboxylic acid methyl ester Utilizing the compound of Step A (13.0 g, 35 mmol, sodium hydride (4.2 g of 60% sodium hydride in mineral oil dispersion, 105 mmol of sodium hydride), methyl iodide (10.9 ml, 175 mmol) and tetrahydrofuran (90 ml) as solvent, the method of Example 1B afforded the title compound (14.15 g) as a yellow amorphous solid.

$^{13}$C NMR (CDCl$_3$): 163.1, 155.5, 151.2, 138.5, 136.8, 131.3, 122.8, 100.8, 51.0, 42.0, 17.6, 13.4.

C. [1-(4-Bromo-2,6-dimethyl-phenyl)-5-dimethyl-amino-3-methylsulfanyl-1H-pyrazol-4-yl]methanol Utilizing the compound of Step B (12.0 g, 30 mmol), diisobutylaluminum hydride (100 ml of a 1.0M toluene solution, 100 mol), and anhydrous tetrahydrofuran (170 ml), the title compound was prepared by the method of Example 2C (3.6 g, isolated as a colorless oil.

$^{13}$C NMR (CDCl$_3$): 151.8, 148.1, 138.7, 137.2, 131.1, 122.3, 106.7, 61.7, 42.6, 17.8, 15.7.

EXAMPLE 4

A. 5-Amino-3-methyl-1-(2,4,6-trichloro-phenyl)-1H-pyrazole-4-carboxylicacid methyl ester To a solution of 2-cyano-3-methyl-3-ethoxy-acrylic acid methyl ester (3.5 g, 0.021 mol) in glacial acetic acid (20 ml), 2,4,6-trichlorophenylhydrazine (4.38 g, 0.021 mol) was added with stirring, followed by triethylamine (2.0 ml, 1.46 g, 0.014 mol). The reaction was refluxed for 13 hours. Solvent removal in vacuo afforded a dark oil, which was dissolved in methylene chloride/water (100 ml of each). The separated organic phase was extracted with an equal volume of water, dried over anhydrous sodium sulfate, and concentrated in vacuo to an orange oil (5.8 g). Flash chromatography of the entire sample (silica gel, 40 micron mesh;

elution with ethyl acetate/hexane=1:3 in volume) afforded the title compound (3.20 g) as a light-orange amorphous solid. Thin layer chromatography (TLC) $R_f$ (silica gel plates, u.v. detection, ethyl acetate/hexane=1:3 in volume): 0.43.

B. 5-Dimethylamino-3-methyl-(2,4,6-trichloro-phenyl)-1H-pyrazole-4-carboxylic acid methyl ester To a well-stirred and ice-bath-chilled solution of the compound of Step A (3.2 g, 9.6 mmol) and methyl iodide (3.0 ml, 6.84 g, 48 mmol) in anhydrous tetrahydrofuran (20 ml), sodium hydride (1.15 g of 60% sodium hydride mineral oil dispersion, 690 mg, 29 mmol of sodium hydride) was added portionwise. The reaction mixture was stirred at 5° C. for 15 minutes; then an ambient temperature for 20 hours. Concentration in vacuo afforded a light-yellow solid, which was dissolved in ethyl acetate/water (100 ml of each) with the pH adjusted to 12 with sodium carbonate. The separated aqueous phase was twice extracted with 50 ml portions of ethyl acetate. The three combined organic extracts were dried over anhydrous sodium sulfate and concentrated in vacuo to afford the title compound (3.5 g) as an orange amorphous solid. TLC $R_f$ (silica gel plates, u.v. detection, ethyl acetate/hexane=1:3 in volume): 0.73.

C. [5-Dimethylamino-3-methyl-1-(2,4,6-trichlorophenyl)-1H-pyrazol-4-yl]-methanol To a well-stirred solution of the compound of Step B (350 mg, 0.96 mmol) in anhydrous tetrahydrofuran (3 ml) chilled to −78° C., diisobutylaluminum hydride (2.90 ml of 1.0M diisobutylaluminum hydride in tetrahydrofuran; 2.9 mmol of diisobutylaluminum hydride) was added dropwise. After stirring for one hour at −78° C. and an additional hour at 5° C., the reaction was stirred at ambient temperature for 2 hours. The reaction was then quenched by dropwise (at 5° C.) addition of methanol (7 ml). The mixture was stirred for 15 minutes at ambient temperature, and then for 10 minutes at 35°–40° C. Concentration in vacuo afforded a yellow solid which was extracted with ethyl acetate (7 ml). The remaining insoluble solids were removed by filtration. The filtrate was extracted with an equal volume of water, dried (anhydrous sodium sulfate), and concentrated in vacuo to afford the title compound as a light-orange oil (0.32 g). The product was used in the next step without further purification.

D. Enantiomeric {2-[5-Dimethylamino-3-methyl-1-(2,4,6-trichlorophenyl)-1H-pyrazol-4-yl-methyl]-1,2,3,4-tetrahydro-isoquinolin-3-yl}-methanol To an ice-bath-chilled, well-stirred solution of the compound of Step C (160 mg, 0.48 mmol and triethylamine (0.08 ml, 0.60 mmol) in anhydrous methylene chloride (3 ml), methanesulfonyl chloride (0.04 ml, 59.2 mg, 0.52 mmol) was added all at once. After 15 minutes of stirring at 5° C. to complete in situ formation of the mesylate of the compound of Step C, the dextrorotatory enantiomer of 3-hydroxymethyl-1,2,3,4-tetrahydroisoquinoline (310 mg, 1.9 mmol), anhydrous N,N-dimethylformamide (0.51 ml) and acetonitrile (1.2 ml) were added. After stirring ½ hour at ambient temperature, the reaction mixture was heated at 55° C. for 19 hours. Concentration in vacuo afforded an orange residue which was dissolved in ethyl acetate/water (100 ml of each) with the pH adjusted to 10 with sodium carbonate. The separated aqueous phase was extracted twice with 50 ml portions of ethyl acetate. The combined organic extracts were dried over anhydrous sodium sulfate and concentrated in vacuo to an orange semi-solid (0.7 g). Flash chromatography of the entire sample (silica gel, 40 micron mesh; eluting with ethyl acetate/hexane=1.3 volume) afforded the title compound (170 mg) as a light-orange oil. $^{13}C$ NMR (CDCl$_3$): 151.6, 151.0, 136.2, 135.3, 135.0, 133.6, 133.3, 129.0, 128.6, 127.0, 126.5, 126.1, 107.5, 62.0, 58.0, 47.6, 45.6, 42.6, 26.2, 13.1.

EXAMPLE 5

A. 2-Cyano-3,3-diethoxy-acrylic acid methyl ester

A reaction mixture consisting of methylcyanoacetate (5.0 ml, 57 mmol) and tetraethylorthocarbonate (17.99 ml, 86 mmol) in acetic anhydride (8.11 ml, 86 mmol) was heated at 130° C. for 5 hours, and then heated at 110° C. for 18 hours. The cooled reaction residue was extracted twice with 125 ml portions of hexane. A hexane-insoluble orange oil containing approximately 40% by weight of the desired compound (as established by NMR inspection) remained. This crude product was used in the next step without further purification. TLC $R_f$ (silica gel plates, u.v. detection, ethyl acetate/hexane=15:85 in volume): 0.13.

B. 5-Amino-3-ethoxy-1-(2,4,6-trichloro-phenyl)-1H-pyrazole-4-carboxylic acid methyl ester The crude product obtained in Step A (4.76 g, containing approximately 1.9 g, 9.6 mmol of 2-cyano-3,3-diethoxy-acrylic acid methyl ester) was combined with 2,4,6-trichlorophenylhydrazine (2.02 g, 9.6 mmol) in ethanol (15 ml). The resulting mixture was refluxed for 18 hours. The solvent was removed in vacuo, and the residue was extracted with methylene chloride/water (100 ml of each) with the pH adjusted to 10 with sodium carbonate. The separated aqueous extract was washed with two 50 ml portions of methylene chloride. The three combined organic extracts were dried over anhydrous sodium sulfate and concentrated in vacuo to an oil (5.98 g). The purity of this crude title compound was significantly improved by flash chromatography (silica gel, 40 micron mesh; elution with ethyl acetate/hexane=15:85 in volume), yielding 910 mg of the title compound as an orange oil. TLC $R_f$ (silica gel plates, u.v. detection; ethyl acetate hexane=15.85 in volume): 0.26. The product was used in the next step without further purification.

C. 5-Dimethylamino-3-ethoxy-1-(2,4,6-trichloro-phenyl)-1H-pyrazole-4-carboxylic acid methyl ester To an ice-bath-chilled solution of the compound of Step B (910 mg, 2.5 mmol) and methyl iodide (778 μl, 12.5 mmol) in anhydrous tetrahydrofuran (10 ml), sodium hydride (300 mg of 60% sodium hydride mineral oil dispersion; 180 mg, 7.5 mmol of sodium hydride) was added portionwise over 5 minutes. The reaction mixture was stirred at ambient temperature for 18 hours. The solvent was removed in vacuo, and the residue was extracted into methylene chloride/water (60 ml of each). The separated aqueous phase was extracted twice with 30 ml portions of methylene chloride. The organic extracts were combined, dried over anhydrous sodium sulfate, and concentrated in vacuo to an amber oil (980 mg). Flash chromatography of the entire sample (silica gel, 40 micron mesh; elution with ethyl acetate/hexane=5.95 in volume) afforded the title compound as a colorless oil (353 mg.)

TLC $R_f$ (silica gel plates, u.v. detection, ethyl acetate/hexane=5:95 in volume): 0.26.

D. [5-Dimethylamino-3-ethoxy-1-(2,4,6-trichlrophenyl)-1H-pyrazol-4-yl]-methanol

Utilizing the procedure of Example 2C, the compound of Step 5C (340 mg, 0.87 mmol) was converted into the corresponding alcohol (230 mg of colorless oil). The product after workup (without chromatography) was used in the next step without further purification.

TLC $R_f$ (silica gel plates, u.v. detection, ethyl acetate/hexane=15:85 in volume): 0.20.

E. Enantiomeric {2-[5-Dimethylamino-3-ethoxy-1-(2,4,6-trichloro-phenyl)-1H-pyrazol-4-ylmethyl]1,2,3,4-tetrahydroisoquinoline -3-yl}-methanol To a well-stirred/ice-bath-chilled methylene chloride (1 ml) solution of the compound of Step 5D (estimated 69 mg, 0.19 mmol) and triethylamine (32 µl, 0.23 mmol), methanesulfonyl chloride (16 µl, 0.21 mmol) was added. After 15 minutes of stirring, the dextrorotatory isomer of 3-hydroxymethyl-1,2,3,4-tetrahydroisoquinoline (124 mg, 0.72 mmol) and anhydrous N,N-dimethylformamide (0.1 ml) were added; and the resulting mixture was heated at 50° C. for 4 hours. After ambient temperature stirring for an additional 48 hours, the solvent was removed in vacuo, and the residue was extracted into methylene chloride/water (60 ml of each) with the pH adjusted to 10 (sodium carbonate). The separated aqueous phase was extracted twice with 30 ml portions of methylene chloride. The combined organic extracts were dried (anhydrous sodium sulfate) and concentrated in vacuo to an oil (410 mg). Flash chromatography of the entire sample (silica gel, 40 micron mesh; elution with ethyl acetate/hexane=1:4 in volume) afforded the title compound (7 mg) as a colorless foam.

$^1$H NMR (CDCl$_3$); (3H, t, J=8 Hz), 2.5–2.8 (7H; 6H, s overlapping with 1H, m), 2.95 (1H, dd), 3.2–4.1 (7H, broad, overlapping multiplets) 4.25 (2H, q, J=8 Hz), 6.96–7.38 (4H, broad m), 7.45 (2H, s).

EXAMPLE 6

Enantiomeric {2-[1-(4-Bromo-2,6-dimethyl-phenyl)-5-dimethylamino-3-methylsulfanyl-1H -pyrazol-4-ylmethyl]-1,2,3,4-tetrahydro-isoquinoline-3-yl}-methanol Utilizing the dextrorotatory isomer of 3-hydroxymethyl-1,2,3,4-tetrahydroisoquinoline (528 mg, 3.24 mmol) dissolved in acetonitrile/anhydrous N,N-dimethylformamide (15 ml and 0.5 ml, respectively) and the situ-generated mesylate of Example 3C (300 mg, 0.81 mmol), triethylamine (169 µl, 1.20 mmol), and methanesulfonyl chloride (81.5 µl, 1.05 mmol) in anhydrous methylene chloride (6 ml)] the title compound (21 mg, 5% yield) was prepared as a colorless amorphous solid by the Example 4D coupling method/workup and flash chromatography (silica gel, 40 micron mesh; elution with ethyl acetate/hexane=1:9 in volume).

TLC $R_f$ (silica gel plates, u.v. detection, ethyl acetate/hexane=1:4 in volume): 0.30. HRMS m/z 514.1402 (M, C$_{25}$H$_{30}$BrN$_4$OS).

EXAMPLE 7

Racemic {2-[5-Dimethylamino-3-methylsulfanyl-1-(2,4,6-trichloro-phenyl)-1H-pyrazol-4-ylmethyl]-1,2,3,4-tetrahydro-isoquinolin-3-yl}-methanol To a stirred solution of the compound of Example 1C (700 mg, 1.9 mmol) and triethylamine (0.304 ml, 2.2 mmol) in anhydrous methylene chloride chilled to 5° C., methanesulfonyl chloride (0.164 ml, 2.1 mmol) was added to form the corresponding mesylate in situ. The reaction mixture was stirred at 5° C. for 25 minutes. A solution of (+)-3-hydroxymethyl-1,2,3,4-tetrahydroisoquinoline (1.24 g, 7.6 mmol) in acetonitrile/anhydrous N,N-dimethylformamide (5 ml and 1.5 ml, respectively) was added, and the reaction mixture was heated with a 55°–60° C. oil bath for 18 hours. The solvent was removed in vacuo, and the residue was dissolved in a ethyl acetate/water mixture (100 ml of each) with the pH adjusted to 9.5 (sodium carbonate). The organic extract was separated, dried over anhydrous sodium sulfate, and concentrated in vacuo to an amber glass. Flash chromatography of the entire sample (silica gel, mesh; elution with ethyl acetate, hexane=1:10 in volume) afforded the title compound (800 mg) as a colorless amorphous solid. $^{13}$C NMR: (CDCl$_3$): 151.8, 149.6, 136.2, 135.5, 134.7, 133.6, 133.4, 129.0, 128.7, 127.1, 126.4, 126.0, 108.7, 62.2, 57.7, 48.3, 45.3, 42.8, 25.9, 14.7.

EXAMPLE 8

Enantiomeric {2-[5-Dimethylamino-3-methylsulfanyl-1-(2,4,6-trichloro-phenyl)-1H-pyrazol-4-ylmethyl]-1,2,3,4-tetrahydro-isoquinolin-3-yl}-methanol To a stirred solution of the compound of Example 1C (258 mg, 0.704 mmol) and triethylamine (0.112 ml, 0.80 mmol) in anhydrous methylene chloride chilled to +5° C., methanesulfonyl chloride (0.061 ml, 0.79 mmol) was added to form the corresponding mesylate in situ. The reaction was stirred at 5° C. for 20 minutes. A solution of the dextrorotatory enantiomer of 3-hydroxymethyl-1,2,3,4-tetrahydroisoquinoline (230 mg, 1.4 mmol) in acetonitrile/anhydrous N,N-dimethylformamide (2.5 ml and 1 ml, respectively) was added, and the resulting mixture was heated with a 60° C. oil bath for 18 hours. The solvent was removed in vacuo and the resulting solid residue was dissolved in methylene chloride/water (25 ml of each) with the pH adjusted to 9.5 (sodium carbonate). The organic phase was separated, washed with an equal volume of water, dried (anhydrous sodium sulfate), and concentrated in vacuo to a solid. The entire sample was pulped in isopropyl alcohol (3 ml). After stirring for 1 hour at ambient temperature, a solid byproduct was filtered. The filtrate was concentrated in vacuo to an oil (0.41 g). Flash chromatography of the entire sample (silica gel, 40 micron mesh; elution with ethyl acetate/hexane=1:5 in volume) afforded the title compound (60 mg) as a colorless amorphous solid.

$^{13}$C NMR (CDCl$_3$): identical to that of the racemic compound prepared in Example 7.

EXAMPLE 9

Enantiomeric {2-[Dimethylamino-3-methylsulfanyl-1-(2,4,6-trichloro-phenyl)-1H-pyrazol-4-ylmethyl]-1,2,3,4-tetrahydro-isoquinolin-3-yl}-methanol Following the procedure of Example 4D, and utilizing the levorotatory enantiomer of 3-hydroxymethyl-1,2,3,4-tetrahydroisoquinoline as the nucleophilic substrate, the title compound was prepared as a colorless amorphous solid.

hu 13C NMR spectrum: identical in all respects to the one for the title (racemic) compound of Example 7.

EXAMPLE 10

Enantiomeric {2-[1-(2,6-Dichloro-4-trifluoromethyl-phenyl)-5-dimethylamino-3-methyl-sulfanyl-1H-pyrazol-4-ylmethyl]-1,2,3,4-tetrahydro-isoquinolin-3-yl}-methanol23

Utilizing the dextrorotatory enantiomer of 3-hydroxymethyl-1,2,3,4-tetrahydroisoquinoline (376 mg, 2.3 mmol) dissolved in acetonitrile/anhydrous N,N-dimethylformamide (1.5 ml and 0.5 ml, respectively) and the in situ-generated mesylate of the compound of Example 2C, the title compound (56 mg) was obtained as a colorless oil by the method of Example 4D and flash chromatography (silica gel, 40 micron mesh; elution with methanol/ methylene chloride=1:4 in volume). TLC $R_f$ (silica gel plates, u.v. detection, methanol/methylene chloride=1,4 in volume): 0.4. HRMS m/z 544.1078 (M, $C_{24}H_{24}Cl_2F_3N_4OS$).

EXAMPLE 11

A. Racemic (2,3-Dihydro-1H-indol-2-yl)-methanol

Racemic 2,3-dihydro-1H-indole-2-carboxylic acid (5.0 g, 30.6 mmol) was suspended in methanol (50 ml). Sodium methoxide (1.66 g, 30.6 mmol) was added, and the resulting slurry was stirred several minutes before the solvent was removed in vacuo. The entire sample was suspended in anhydrous tetrahydrofuran (60 ml). Lithium aluminum hydride (1.0M solution in tetrahydrofuran; 30.6 ml, 30.6 mmol) was added dropwise over 15 minutes. The reaction mixture was refluxed for 3 hours. The ice-bath-chilled mixture was then cautiously quenched by dropwise addition of 15 percent aqueous sodium hydroxide (4 ml). The reaction was filtered, and the filtrate was concentrated in vacuo to afford (+)-2-hydroxymethyl-indoline (3.69 g) as a viscous brown oil, used in the next step without further purification. TLC $R_f$ (silica gel plates; u.v. detection, elution with ethyl acetate/hexane=1:4 in volume): 0.15.

B. Racemic {1-[5-Dimethylamino-3-methylsulfanyl-1-(2,4,6-trichloro-phenyl)-1H-pyrazol-4-ylmethyl]-2,3-dihydro-1H-indol-2-yl}-methanol By the procedure of Example 4D, the racemic mixture of Step A (895 mg, 6 mmol) was reacted with the in situ prepared mesylate derived from 500 mg (1.5 mmol) of the compound of Example 1C. Flash chromatography (silica gel, 40 micron mesh, eluting with ethyl acetate/hexane=1:4 in volume) of the crude product after workup as described in Example 4D afforded the title compound as a colorless oil (124 mg).

$^{13}$C NMR (CDCl$_3$): 153.0, 150.7, 148.6, 136.2, 135.7, 135.0, 129.6, 128.7, 127.2, 124.5, 119.2, 109.7, 108.9, 67.8, 63.1, 45.1, 42.8, 31.7, 14.4.

EXAMPLE 12

A. 2-Benzyl-4H-isoquinoline-1,3-dione

A mixture consisting of homophthalic acid (25 g, 0.139 mol) and benzylamine (15.2 ml, 14.91 g, 0.139 mol) was heated at 165°–180° C. for two hours, producing a vigorous release of water vapor. Cooling afforded a hard green solid which was pulverized, triturated with diethyl ether, and isolated by filtration to afford the title compound as a light-green granular solid (29.4 g) used in the next step without further purification.

TLC $R_f$ (silica gel plates; u.v. detection, eluting with ethyl acetate/hexane=15:85 in volume): 43; $^{13}$C NMR (CDCl$_3$): 169.9, 164.8, 137.1, 134.1, 133.7, 129.3, 129.0, 128.4, 127.7, 127.5, 127.1, 125.4, 43.3, 36.5.

B. Racemic 2-Benzyl-3-hydroxy-3,4-dihydro-2H-isoquinoline-1-one

To a well-stirred ice-bath-chilled solution of 2-benzyl-4H-isoquinoline-1,3-dione (5.0 g, 20 mmol) in methanol (40 ml), sodium borohydride (3.0 g, 80 mmol) was added portionwise over 20 minutes. The reaction mixture was stirred at ambient temperature for 48 hours. TLC inspection of a reaction aliquot confirmed substantial formation of product, with some starting material remaining. TLC $R_f$ of the title compound (silica gel plates; u.v. detection; elution with ethyl acetate/hexane=3.7 in volume): 0.24. The ice-bath-chilled reaction mixture was cautiously quenched with water (3 ml). Anhydrous sodium sulfate was added to dry the mixture, which was then filtered. The filtrate was concentrated in vacuo to a dark green oil (3.5 g). Flash chromatography (silica gel, 40 micron mesh; elution with ethyl acetate hexane=3.7 volume) afforded the title compound as a colorless amorphous solid (1.35 g). The labile material was used immediately in the next step.

C. Racemic (2-Benzyl-1-oxo-1,2,3,4-tetrahydro-isoquinolin-3-yl)-acetic acid methyl ester Sodium hydride (307 mg of 60% sodium hydride mineral oil dispersion; 184 mg, 7.7 mmol of sodium hydride) was added portionwise over several minutes to a well-stirred, ice-bath-chilled solution of the racemic mixtures of Step B (1.35 g, 5.34 mmol) in anhydrous tetrahydrofuran (20 ml). Methyl diethylphosphonoacetate (1.76 ml, 2.015 g, 9.6 mmol) was added portionwise over several minutes, and the resulting mixture was then stirred for 24 hours at ambient temperature. The solvent was removed in vacuo, and the residue was dissolved in ethyl acetate/water (50 ml of each). The separated aqueous extract was extracted twice with 10 ml portions of ethyl acetate. The combined organic extracts were dried over anhydrous sodium sulfate and concentrated in vacuo to a brown oil (2.4 g). Flash chromatography of the entire sample (silica gel, 40 micron mesh; elution with ethyl acetate/hexane=15:85 in volume) afforded the title compound (650 mg), as a colorless viscous oil.

$^{13}$C NMR (CDCl$_3$): 171.3, 163.7, 137.8, 135.6, 132.2, 128.9, 128.7, 128.3, 128.1 (2), 127.6, 127.3, 51.8, 51.7, 48.7, 36.2, 32.5.

D. Racemic 2-(2-Benzyl-1,2,3,4-tetrahydro-isoquinolin-3-yl)-ethanol

To a well-stirred ice-bath-chilled solution of the racemic mixture of Step C (650 mg, 2.0 mmol) in anhydrous tetrahydrofuran (10 ml), a solution of lithium aluminum hydride in tetrahydrofuran (6.11 ml of a 1.0M solution, 6.11 mmol of lithium aluminum hydride) was added dropwise over 5 minutes. The reaction mixture was then stirred for 24 hours at ambient temperature before being ice-bath-chilled and cautiously quenched with 15% aqueous sodium hydroxide (2 ml). Anhydrous sodium sulfate was added to dry the mixture, which was then filtered. The filtrate was concentrated in vacuo to afford the title compound as a colorless oil in quantitative yield.

TLC $R_f$ (silica gel plates; u.v. detection, elution with ethyl acetate/hexane=1:4 in volume): 0.21.

E. Racemic 2-(1,2,3,4-Tetrahydro-isoquinolin-3-yl)-ethanol (+)-2-(2-Benzyl-1,2,3,4-tetrahydro-isoquinolin-3-yl)-ethanol (610 mg, 2.3 mmol) was hydrogenated at 40 p.s.i.g. on a Parr Apparatus (305 mg of 10% palladium-on-carbon catalyst; methanol/concentrated hydrochloric acid solvent (15 ml and 0.25 ml, respectively) for 5 hours. The catalyst was filtered, and the filtrate was concentrated in vacuo to an oil, which was dissolved in dilute aqueous (pH 9) sodium carbonate/methylene chloride (50 ml of each). The aqueous phase was separated and extracted with two 10 ml portions of methylene chloride. The combined organic extracts were dried over anhydrous sodium sulfate and concentrated in vacuo to afford the title compound as a viscous colorless oil (quantitative yield).

$^{13}$C NMR (CDCl$_3$): 135.4, 134.2, 129.3, 126.3, 126.1, 125.9, 63.2, 55.5, 47.9, 37.2, 35.5.

F. Racemic 2-{2-[5-Dimethylamino-methylsulfanyl-1-(2,4,6-trichloro-phenyl)-1H-pyrazol-4-ylmethyl]-1,2,3,4-tetrahydro-isoquinolin-3-yl}-ethanol Racemic 2-(1,2,3,4-tetrahydro-isoquinolin-3-yl)-ethanol (400 mg, 2.4 mmol) was reacted with the in situ-prepared mesylate of the compound of Example 1C by the method of Example 4D affording the title compound (80 mg) as a colorless viscous oil.

$^{13}$C NMR (CDCl$_3$): 151.9, 149.8, 136.2, 135.5, 134.8, 133.1 (2), 129.3, 128.7, 126.9, 126.2, 126.0, 108.0, 62.3, 55.3, 48.0, 46.1, 42.3, 32.5, 29.1, 14.8.

EXAMPLE 13

[4-(3-Butoxymethyl-3,4-dihydro-1H-isoquinolin-2-ylmethyl)-5-methyl-sulfanyl-2-(2,4,6-trichloro-phenyl)-2H-pyrazol-3-yl)]-dimethyl-amine To an anhydrous tetrahydrofuran (2 ml) solution of the racemic mixture of Example 7 (0.21 g, 0.41 mmol), sodium hydride (82 mg of 60% sodium hydride mineral oil dispersion; 49 mg, 2.0 mmol of sodium hydride) was added, and the resulting mixture was stirred 10 minutes before adding n-butyliodide (0.19 ml, 307 mg, 1.7 mmol). The reaction mixture was stirred for 24 hours. Thin layer chromatography inspection of a reaction aliquot showed incomplete reaction. More sodium hydride (82 mg of 60% sodium hydride mineral oil dispersion; 49 mg, 2.0 mmol of sodium hydride), anhydrous tetrahydrofuran (0.5 ml), and n-butyliodide (0.19 ml, 307 mg, 1.7 mmol) was added; and the resulting mixture was stirred 24 hours at ambient temperature to essentially complete reaction. The solvent was removed in vacuo and the residue was dissolved in ethyl acetate/water (50 ml of each). The separated aqueous extract was extracted with three 10 ml portions of ethyl acetate. The combined organic extracts were dried (anhydrous sodium sulfate) and concentrated in vacuo to a viscous orange oil (0.3 g). Chromatography involving sequential flash and then gravity methods of elution (silica gel, 40 micron mesh; elution with ethyl acetate/hexane=1:0 in volume) afforded the title compound (150 mg), as a viscous yellow oil.

$^{13}$C NMR (CDCl$_3$): 152.0, 149.9, 136.1, 135.3, 134.9, 134.7, 134.0, 129.1, 128.6, 126.4, 126.0, 125.5, 109.4, 71.1, 69.8, 56.2, 50.4, 47.9, 42.4, 31.9, 30.8, 19.4, 15.2, 13.9.

EXAMPLE 14

Racemic [4-(3-Methoxymethyl-3,4-dihydro-1H-isoquinolin-2-ylmethyl)-5-methylsulfanyl-2-(2,4,6-trichloro-phenyl)-2H-pyrazol-3-yl]-dimethyl-amine To a solution of the racemic mixture of Example 7 (200 mg, 0.39 mmol) in anhydrous tetrahydrofuran (2.0 ml), sodium hydride (78 mg of 60% sodium hydride mineral oil dispersion; 46 mg, 2.0 mmol of sodium hydride) was added; and the resulting mixture was stirred for 15 minutes at ambient temperature. Methyl iodide (0.10 ml, 1.6 mmol) was added, and the mixture was stirred for 18 hours at ambient temperature. The solvent was removed in vacuo, and the residue was dissolved in ethyl acetate/water (20 ml of each). The aqueous phase was separated and extracted with three equal volumes of ethyl acetate. The combined organic extracts were dried (anhydrous sodium sulfate) and concentrated in vacuo to a yellow oil. Flash chromatography of the entire sample (silica gel, 40 micron mesh; elution with ethyl acetate/hexane=1:10 in volume) afforded the title compound (118 mg) as a light-yellow oil.

$^{13}$C NMR (CDCl$_3$): 152.0, 149.8, 136.1, 135.3, 134.8, 134.6, 133.9, 129.1, 128.6, 126.5, 126.1, 125.6, 109.2, 71.8, 58.9, 56.0, 50.6, 47.6, 42.4, 30.6, 15.2.

EXAMPLE 15

Enantiomeric [4-(3-Methoxymethyl-3,4-dihydro-1H-isoquinolin-2-ylmethyl)-5-methylsulfanyl-2-(2,4,6-trichloro-phenyl)-2H-pyrazol-3-yl]-dimethyl-amine To a well-stirred solution of the compound of Example 8 (200 mg, 0.39 mmol) in anhydrous tetrahydrofuran (3 ml), sodium hydride (78 mg of 60% sodium hydride mineral oil dispersion, 46.8 mg, 2.0 mmol of sodium hydride) was added. The mixture was stirred for 5 minutes at ambient temperature before methyl iodide (0.097 ml, 1.6 mmol) was added. After stirring for 16 hours at ambient temperature, the solvent was removed in vacuo, and the residue was extracted in to an ethyl acetate/water (60 ml of each) mixture. The separated aqueous phase was then extracted with three equal volume portions of fresh ethyl acetate. The combined ethyl acetate extracts were dried (anhydrous sodium sulfate) and concentrated in vacuo to an orange oil (510 mg). Flash chromatography of the entire sample (silica gel, 40 micron mesh; elution with ethyl acetate/hexane=1:10 in volume) afforded the single enantiomeric title product as a light-yellow oil (50 mg, 24% yield). The TLC R$_f$ data and $^1$H NMR $^{13}$C NMR spectra were identical in all respects to those obtained with the corresponding racemic product obtained by Example 14.

EXAMPLE 16

Enantiomeric [4-(3-isopropoxymethyl-3,4-dihydro-1H-isoquinolin-2-ylmethyl)-5-methylsulfanyl-2(2,4,6-trichloro-phenyl)-2H-pyrazol-3-yl]-dimethyl-amine To a well-stirred solution of the compound of Example 8 (310 mg, 0.61 mmol) in anhydrous tetrahydrofuran (3 ml), sodium hydride (140 mg of 60% sodium hydride mineral oil dispersion, 84 mg, 3.5 mmol of sodium hydride) was added. The reaction mixture was stirred at ambient temperature for 5 minutes before isopropyl iodide (0.42 ml, 4.2 mmol) was added. The reaction was then stirred at ambient temperature for 23 hours. Additional anhydrous tetrahydrofuran (1 ml) and sodium hydride (120 mg of 60% sodium hydride mineral oil dispersion, 72 mg, 3.0 mmol of sodium hydride) were added, followed 5 minutes later by a second portion of isopropyliodide (0.30 ml, 3.0 mmol). Ambient temperature stirring was continued for an additional 5 hours. The solvent was removed in vacuo, and the residue was extracted with ethyl acetate/water (60 ml of each). The separated aqueous phase was extracted twice with 30 ml portions of fresh ethyl acetate. The combined organic extracts were dried over anhydrous sodium sulfate and concentrated in vacuo to afford an orange oil (600 mg). Chromatography (silica gel, 40 micron mesh; elution with ethyl acetate/hexane=1:10 in volume) afforded the title compound (2.0 mg) as a light-yellow oil. The TLC R$_f$ and NMR spectral properties of the title compound are identical in all respects to those of the racemic counterpart prepared by Example 17.

EXAMPLE 17

Racemic [4-(3-isopropoxymethyl-3,4-dihydro-1H-isoquinolin-2-ylmethyl)-5-methylsulfanyl-2-(2,4,6-trichloro-phenyl)-2H-pyrazol-3-yl]-dimethyl-amine Utilizing the procedure of Example 15, the compound of Example 7 (215 mg, 0.42 mmol) in anhydrous tetrahydrofuran (2 ml) was reacted first with sodium hydride (100 mg of 60% sodium hydride mineral oil dispersion; 60 mg, 2.5 mmol of sodium hydride), and then with isopropyl iodide (0.29 ml, 497 mg, 2.9 mmol), affording the title compound (20 mg) as a yellow oil.

$^{13}$C NMR (CDCl$_3$): 152.1, 149.7, 136.1, 135.3, 134.7 (2), 134.0, 129.1, 128.6, 126.4, 126.0, 125.5, 109.4, 71.9, 67.0, 56.6, 50.3, 48.0, 42.4, 30.9, 22.3, 22.1, 15.2.

EXAMPLE 18

Racemic Dimethyl-{4-[3-(3-methyl-butoxymethyl)-3,4-dihydro-1H-isoquinolin-2-ylmethyl]-5-methylsulfanyl-2-(2,4,6-trichloro-phenyl)-2-pyrazol-3-yl}-amine Utilizing the procedure of Example 16, the compound of Example 7 (210 mg, 0.41 mmol) in anhydrous tetrahydrofuran (2 ml) was reacted first with sodium hydride (100 mg of 60% sodium hydride mineral oil dispersion; 60 mg, 2.5 mmol of sodium hydride), and then with isopentyl iodide (570 mg, 2.9 mmol), affording the title compound (44 mg) as a yellow oil.

$^{13}$C NMR (CDCl$_3$): 152.0, 149.9, 136.1, 135.3, 134.7 (2), 134.0, 129.1, 128.6, 126.4, 126.0, 125.5, 109.3, 69.8, 56.2, 50.3, 47.9, 42.4, 38.6, 30.9, 25.1, 22.7, 22.6, 15.2.

EXAMPLE 19

Racemic {4-[3-(2-Methoxy-ethoxymethyl)-3,4-dichloro-1H-isoquinolin-2-ylmethyl]-5-methylsulfanyl-2-(2,4,6-trichloro-phenyl)-2H-pyrazol-3-yl}-dimethyl-amine To a solution of the compound of Example 7 (64 mg, 0.12 mmol) in anhydrous tetrahydrofuran (0.5 ml), sodium hydride (17.5 mg of 60% sodium hydride mineral dispersion; 10.5 mg, 0.44 mmol of sodium hydride) was added; and the resulting mixture was stirred for 15 minutes. 1-iodo-2-methoxy-ethane (0.1 ml, 0.5 mmol) was added. After stirring for 48 hours followed by 6 hours at reflux, thin layer chromatography inspection of an aliquot showed incomplete reaction. Additional sodium hydride (33 mg of 60% mineral oil dispersion, 20 mg, 1.0 mmol of sodium hydride), 1-iodo-2-methoxyethane (100 μl, 0.5 mmol) and anhydrous tetrahydrofuran (0.8 ml) were added; and the mixture was refluxed for 18 hours to complete reaction. The solvent was removed in vacuo, and the residue was dissolved in ethyl acetate/water (20 ml of each). The separated aqueous phase was extracted with three equal volumes of ethyl acetate. The combined organic extracts were dried over anhydrous sodium sulfate and concentrated in vacuo to afford an orange gum. Flash chromatography (silica gel, 40 micron mesh; elution with ethyl acetate/hexane=1:4 in volume) afforded the title compound (23 mg) as a light-yellow oil.

$^{13}$C NMR (CDCl$_3$): 152.1, 149.7, 136.3, 135.4, 134.7 (2), 134.0, 129.1, 128.6, 126.5, 126.0, 125.5, 109.4, 72.0, 70.5, 70.3, 59.1, 56.0, 50.2, 47.9, 42.4, 30.7, 15.2.

EXAMPLE 20

Enantiomeric2-{2-[5-Dimethylamino-3-methylsulfanyl-1-(2,4,6-trichloro-phenyl)-1H-pyrazol-4-ylmethyl]-1,2,3,4-tetrahydro-isoquinolin-3-ylmethoxy}-ethanol and the corresponding tert-butyl-dimethylsilyl ether To a solution of the compound of Example 8 (100 mg, 0.195 mmol) in anhydrous tetrahydrofuran (0.2 ml), sodium hydride (18.4 mg of 60% sodium hydride mineral oil dispersion, 11.04 mg, 0.46 mmol of sodium hydride) was added; and the resulting mixture was stirred for 5 minutes at ambient temperature before adding 1-iodo-2-(tert-butyldimethylsilyloxy)ethane (222 mg, 0.39 mmol). The reaction was then heated at 85° C. for 2.5 hours. Thin layer chromatography of a reaction aliquot indicated alkylation to be complete. The solvent was removed in vacuo and the residue was dissolved in an ethylacetate/water mixture (50 ml of each). The separated organic extract was then dried over anhydrous sodium sulfate and concentrated in vacuo to a yellow oil (285 mg). Flash chromatography purification of the entire sample (silica gel, 40 micron mesh; eluting with ethylacetate/hexane=2.5:97.5 in volume) afforded the purified silylated title compound (14 mg) as a colorless oil.

$^{13}$C NMR (CDCl$_3$): ppm 152.0, 149.9, 136.1, 135.3, 134.8, 134.6, 133.9, 129.1, 128.6, 126.4, 126.0, 125.5, 109.3, 72.7, 70.3, 62.7, 56.2, 50.5, 47.7, 42.4, 30.6, 25.9, 22.6, 18.4, 15.2. The entire sample of silylated title compound (14 mg, 0.021 mmol) was dissolved in tetrahydrofuran. Tetrabutylammonium fluoride (42 μl of a 1.00M solution in tetrahydrofuran, 0.042 mmol) was added, and the resulting mixture was stirred for 1 hour at ambient temperature. Thin layer chromatography revealed the presence of a small amount of the silylated compound. An additional 4 μl of 1.0M tetrabutylammonium fluoride in tetrahydrofuran effected complete desilylation within 30 minutes. The solvent was removed in vacuo, and the residue was dissolved in an ethylacetate/water (20 ml of each) mixture. The layers were separated, and the aqueous portion was extracted twice with 10 ml portions of fresh ethyl acetate. The combined organic extracts were dried over anhydrous sodium sulfate and concentrated to an oil (20 mg). Flash chromatography of the entire sample (silica gel, 40 micron mesh; elution with ethylacetate/hexane=1:3 in volume) afforded the first title compound (11.5 mg) as a colorless oil.

TLC R$_f$ (silica gel plates; u.v. detection, ethylacetate/hexane=1:3 in volume): 0.20.

EXAMPLE 21

1-[5-Dimethylamino-3-methylsulfanyl-1-(2,4,6-trichloro-phenyl)-1H-pyrazol-4-yl-methyl]-naphthalen-2-ol and Dimethyl-[5-methylsulfanyl-4-(naphthalene-2-yloxymethyl)-2-(2,4,6-trichloro-phenyl)-2H-pyrazol-3-yl]-amine Utilizing the procedure of Example 4D, the mesylate of the compound of Example 1C (3 mmol) was prepared in situ in anhydrous methylene chloride (12 ml). Separately, sodium hydride (480 mg of 60% sodium hydride mineral oil dispersion, 288 mg, 12 mmol of sodium hydride) was added portionwise over several minutes to a stirred solution of 2-napthol (1.73 g, 12 mmol)in anhydrous N,N-dimethylformamide (4 ml). After stirring at ambient temperature for 20 minutes, the sodium salt of the 2-napthol/N,N-dimethylformamide mixture was added to the above-prepared mesylate/methylene chloride solution. The resulting mixture was stirred at 50° C. for 18 hours. The solvents were removed in vacuo and the residue was extracted into ethylacetate/water (60 ml of each), with the pH adjusted to 6 (1N aqueous hydrochloric acid). The separated aqueous phase was extracted with 60 ml of fresh ethyl acetate. The combined organic extracts were extracted with an equal volume of water, dried over anhydrous sodium sulfate and concentrated in vacuo to afford an amber oil (2.9 g). Flash chromatography of the entire sample (silica gel, 40 micron mesh; elution with ethylacetate/hexane=1:9 in volume) afforded the first title compound (the product of C-alkylation; 388 mg) as a colorless foam, and the second title compound (the product of O-alkylation; 46 mg) as a colorless oil.

The first title compound (product of C-alkylation): $^{13}$C NMR (CDCl$_3$): 152.9, 149.1, 148.2, 136.5 (2), 135.1, 133.2, 129.4, 128.9, 128.6, 128.5, 126.1, 123.7, 123.0, 119.5, 118.0, 113.0, 42.7, 19.6, 16.0.

The second title compound (product of O-alkylation): $^{13}C$ NMR (CDCl$_3$): 156.5, 153.4, 149.7, 136.1, 135.6, 134.6, 129.4, 129.1, 128.7, 127.7, 126.8, 126.4, 123.8, 119.3, 107.3, 107.0, 60.5, 42.6, 15.7.

EXAMPLE 22

Dimethyl-(5-methylsulfanyl-4-phenoxymethyl-2-(2,4,6-trichloro-phenyl)-2H-pyrazol-3-yl]-amine and 2-[5-Dimethylamino-3-methylsulfanyl-1-(2,4,6-trichloro-phenyl)-1H-pyrazol-4-ylmethyl]-phenol To a solution of phenol (564 mg, 6.0 mmol) in anhydrous N,N-dimethylformamide (1.0 ml), sodium hydride (240 mg of 60% sodium hydride mineral oil dispersion; 144 mg, 6.0 mmol of sodium hydride) was added portionwise over 5 minutes. The mixture was then stirred for 15 minutes at ambient temperature. Separately-utilizing the general procedure of Example 4D, the mesylate of the compound of Example 1C (1.5 mmol) was prepared in situ in anhydrous methylene chloride (6 ml). The entire phenol sodium salt/N,N-dimethylformamide sample was added all at once to the above-prepared (well-stirred/ice-bath-chilled) mesylate solution: and the resulting mixture was heated at 50° C. for 18 hours. The solvent was removed in vacuo and the resulting residue was extracted into ethylacetate/water (60 ml of each) with the pH of the aqueous phase adjusted to 6.0 (1N hydrochloric acid). The separated aqueous phase was twice extracted with 30 ml portions of fresh ethyl acetate. The organic extracts were combined, extracted with an equal volume of water, dried over anhydrous sodium sulfate, and concentrated in vacuo to a solid (900 mg). Flash chromatography (silica gel, 40 micron mesh; elution with ethylacetate/hexane=1:9 in volume) of the entire sample afforded an impure sample (90 mg) of the C-alkylated title compound, and a likewise partially-purified sample (190 mg) of O-alkylated title compound. Final purification of both compounds by separate silica gel flash chromatography of each sample (elution with hexane/methylene chloride=2:3 in volume) afforded 11 mg and 58 mg respectively, of the C-alkylated title compound and the O-alkylated title compound.

The second title compound (product of C-alkylation): $^{13}C$ NMR (CDCl$_3$): 154.4, 149.4, 149.0, 136.4, 136.1, 135.0, 130.2, 128.8, 127.8, 126.1, 120.3, 116.1, 111.2, 42.7, 24.2, 15.2.

The first title compound (product of O-alkylation): $^{13}C$ NMR (CDCl$_3$): 158.6, 153.1, 149.5, 136.1, 135.6, 134.5, 129.5, 128.7, 121.0, 115.1, 107.2, 60.4, 42.6, 15.7.

EXAMPLE 23

[4-(2-Methoxy-naphthalen-1-ylmethyl)-5-methylsulfanyl-2-(2,4,6-trichloro-phenyl)-2H-pyrazol-3-yl]-dimethyl-amine To a well-stirred solution of the first title compound of Example 21 (121 mg, 0.25 mmol) in anhydrous tetrahydrofuran (1.0 ml), sodium hydride (25 mg of 60% sodium hydride mineral oil dispersion; 15 mg, 0.63 mmol of sodium hydride) was added portionwise over 5 minutes. After stirring the mixture for 10 minutes at ambient temperature, methyl iodide (78 µl, 1.25 mmol) was added. The reaction mixture was stirred 1 hour (ambient temperature) before a second portion of methyl iodide (78 µl, 1.25 mmol) was added. The reaction was stirred for 18 hours at ambient temperature before in vacuo removal of solvent. The residue was extracted into ethylacetate/water (60 ml of each), The separated aqueous extract was extracted twice with 30 ml portions of fresh ethyl acetate. The combined organic extracts were dried over anhydrous sodium sulfate and concentrated in vacuo to afford a yellow oil (138 mg). Flash chromatography, using the entire sample (silica gel, 40 micron mesh; elution with ethyl acetate/hexane=1:9 in volume) afforded the title compound (74 mg) as a colorless amorphous solid.

$^{13}C$ NMR (CDCl$_3$): 154.9, 149.9, 148.4, 136.3 (2), 135.3, 133.5, 129.3, 128.5, 128.4, 128.3, 125.9, 124.2, 123.3, 121.1, 113.5, 112.7, 56.5, 41.7, 19.8, 15.2.

EXAMPLE 24

[4-(2-isopropoxy-naphthalen-1-ylmethyl)-5-methylsulfanyl-2-(2,4,6-trichlorophenyl)-2H-pyrazol-3-yl]-dimethyl-amine To a well-stirred solution of the first title compound of Example 21 (120 mg, 0.24 mmol) in anhydrous tetrahydrofuran (1.0 ml), sodium hydride (29 mg of 60% sodium hydride mineral oil dispersion; 17.4 mg, 0.73 mmol of sodium hydride) was added portionwise over 5 minutes. After stirring the mixture at ambient temperature for 30 minutes, 2-iodopropane (192 µl, 1.92 mmol) was added; and the resulting mixture was stirred (ambient temperature) for 18 hours. TLC inspection of a reaction aliquot indicated incomplete reaction. A second portion of 2-iodopropane (200 µl, 2.0 mmol) was added, and the mixture was stirred for an additional 18 hours. The solvent was removed in vacuo and the residue was extracted into ethyl acetate/water (60 ml of each). The separated aqueous layer was extracted twice with 20 ml portions of fresh ethyl acetate. The combined organic extracts were dried over anhydrous sodium sulfate and concentrated in vacuo to afford a yellow oil (161 mg). Flash chromatography (silica gel, 40 micron mesh; elution with ethyl acetate/hexane=5:95 in volume) afforded the title compound (70 mg) as a colorless foam.

$^{13}C$ NMR (CDCl$_3$): 153.4, 150.0, 148.4, 136.3 (2), 135.2, 133.8, 129.4, 128.4, 128.2, 128.1, 125.7, 124.5, 123.3, 116.2, 112.8, 71.6, 41.6, 22.6, 20.1, 15.3.

EXAMPLE 25

4-[5-Dimethylamino-3-methylsulfanyl-1-(2,4,6-trichlorophenyl)-1H-pyrazol-4-yl-methyl]-4H-isoquinoline-1,3-dione To a well-stirred suspension of homophthalimide (467 mg, 2.9 mmol) in anhydrous N,N-dimethylformamide (1.8 ml), sodium hydride (128 mg of 60% sodium hydride mineral oil dispersion, 76.8 mg, 3.2 mmol of sodium hydride) was added all at once. The resulting mixture was heated at 65° C. for 20 minutes. Utilizing the method of Example 4D, the compound of Example 1C (1.9 mmol) was prepared in situ. With both mixtures chilled to 5° C., the entire sodium homophthalimide N,N-dimethylformamide sample and mesylate solution were combined. Acetonitrile (5 ml) was added, and the mixture was heated for 18 hours at 65° C. The solvents were removed in vacuo to afford a solid which was extracted into methylene chloride/water (100 ml of each), with the pH adjusted to 9.0. The separated organic phase was extracted with an equal volume of dilute aqueous sodium carbonate (pH 9); and then extracted with an equal volume of water. Anhydrous sodium sulfate drying and concentration in vacuo afforded a foam (909 mg).

Crystallization of the entire sample from isopropyl alcohol (30 ml) afforded 140 mg (14.4% yield) of the title compound (colorless crystals, m.p. 186°–187° C.).

EXAMPLE 26

2-[5-Dimethylamino-3-methylsulfanyl-1-(2,4,6-trichlorophenyl)-1H-pyrazol-4-ylmethyl]-isoindole-1,3-dione To a well-stirred ice-bath-chilled solution of phthalimide (427 mg, 2.9 mmol) in anhydrous N,N-dimethylformamide (4 ml), sodium hydride (128 mg of 60% sodium hydride mineral oil dispersion, 77 mg, 3.2 mmol of sodium hydride) was added. The resulting mixture was stirred at ambient temperature for 20 minutes. Separately, to an ice-bath-chilled solution of the compound of Example 1C (700 mg, 1.9 mmol) and triethylamine (304 µl, 2.2 mmol) in anhydrous methylene chloride (9 ml), methanesulfonyl chloride (104 µl, 2.1 mmol) was added all at once; and the resulting mixture was stirred (5° C.) for 15 minutes to complete the in situ formation of the mesylate of the compound of Example 1C. While stirring the freshly prepared mesylate solution (5° C.), the entire sodium phthalimide/N,N-dimethylformamide mixture (also chilled to 5° C.), was added all at once; and the resulting reaction mixture was gently refluxed for 18 hours. The solvent was removed in vacuo, and the residue was extracted into methylene chloride/dilute aqueous sodium bicarbonate (pH 8; 100 ml of each). The separated organic phase was dried over magnesium sulfate and concentrated in vacuo to an oil (762 mg). Flash chromatography with the entire sample (30 g silica gel, 40 micron mesh; elution with ethyl acetate/hexane in volume ratios of 6:94, 8:92, 12:88, and 1:4, respectively for each of four successively-collected 250 ml volumes of eluent) afforded the title compound (160 mg), as a colorless amorphous solid.

$^{13}$C NMR (CDCl$_3$): 167.8, 151.7, 148.6, 136.3, 135.6, 134.7, 133.9, 132.1, 128.6, 123.3, 106.4, 42.5, 31.9, 15.0.

EXAMPLE 27

A. 5-Amino-1-(2,6-dichloro-4-trifluoromethyl-phenyl)-3-ethyl-1H-pyrazole-4-carboxylic acid methyl ether A solution consisting of 2-cyano-3-ethyl-3-ethoxy-acrylic acid methyl ester (20.14 g, 109 mmol) and 2,6-dichloro-4-trifluoromethylphenylhydrazine (26.93 g, 109 mmol) in glacial acetic acid (42 ml) was heated at reflux for 4 hours; and then allowed to stir at ambient temperature for 18 hours. The solvent was removed in vacuo and the residual oil was extracted into 150 ml of ethyl acetate. Residual acetic was removed from the extract by mixing with aqueous saturated sodium bicarbonate. The separated ethyl acetate extract was dried (anhydrous sodium sulfate and concentrated in vacuo to a brown oil (47 g). Flash chromatography of the entire sample (silica gel; 40 micron mesh; elution with ethylacetate/hexane =15:85 in volume) afforded the title compound (19.5 g) as a waxy solid. TLC R$_f$(silica gel plates; u.v. detection; ethylacetate/hexane=15:85 in volume): 0.30.

$^{13}$C NMR (CDCl$_3$): 165.2, 157.0, 151.5, 137.0, 127.5, 126.1 (2), 123.8, 120.4, 116.7, 93.2, 50.8, 22.1, 12.8.

B. 1-(2,6-Dichloro-4-trifluoromethyl-phenyl)-5-dimethylamino-3-ethyl-1H-pyrazole-4-carboxylic acid methyl ester By the general method of Example 4B, utilizing 19.4 g (52 mmol) of the compound of Step A, the title compound was prepared and isolated as an orange oil (22.73 g). TLC R$_f$ (silica gel plates; u.v. detection; ethylacetate/hexane =15:85 in volume): 0.73.

$^{13}$C NMR (CDCl$_3$) 163.7, 158.6, 156.5, 136.3, 127.6, 125.8, 125.7, 124.0, 120.4, 116.8, 102.4, 51.0, 42.1, 22.7, 13.0.

C. [1-(2,6-Dichloro-4-trifluoromethyl-dimethylamino-3-ethyl-1H-pyrazol-4-yl]-methanol To a dry ice-acetone bath chilled solution of the Step B compound (9.0 g, 22.6 mmol) in anhydrous tetrahydrofuran (80 ml), a 1.0M solution of diisobutylaluminum hydride (75 ml, 75 mmol of diisobutylaluminum hydride) was added dropwise over 5 minutes. The reaction was then stirred at 5° C. (icebath) for 30 minutes. The reaction mixture was quenched by addition of water (4.5 ml) and stirred for 10 minutes prior to warming to about 50° C. The solvent was removed from the now heterogeneous (gelatinous) mixture in vacuo. The residue was pulped with ethyl acetate (100 ml), and the mixture filtered through celite. The filtrate solvent was removed in vacuo. The resulting residue was pulped with 40 ml of an ethylacetate/hexane (1:9 in volume) mixture, affording a colorless solid which was filtered and dried (5.1 g). Further purification of the entire sample by three successive pulpings in 20 ml of hexane (and product isolation by filtration) afforded the title compound (3.6 g) as a colorless solid. TLC R$_f$ (silica gel plates; u.v. detection; ethylacetate/hexanes=1:4 in volume): 0.40.

$^{13}$C NMR (CDCl$_3$): 156.5, 152.1, 136.5, 127.7, 125.7 (2), 124.1, 120.5, 116.9, 106.7, 61.4, 43.1, 20.6, 13.4.

D. 8-[1-(2,6-Dichloro-4-trifluoromethyl)-5-dimethylamino-3-ethyl-1H-pyrazol-4-ylmethyl]-quinolin-7-ol By the general method of Example 21, and utilizing 7-hydroxyquinoline (237 mg, 1.63 mmol) in place of 2-napthol as the nucleophilic reactant and the in situ formed mesylate of the Step C compound as the substrate, the title compound (the product of C-alkylation, 208 mg) was prepared and isolated as a light yellow amorphous solid. TLC R$_f$ (silica gel plates; u.v. detection, ethylacetate/hexane=1:4 in volume): 0.36. HRMS m/z 509.10872 (M+1, C$_{24}$H$_{22}$N$_4$OCl$_2$F$_3$).

EXAMPLE 28

Enantiomeric {2-[1-(2,6-Dichloro-4-trifluoromethylphenyl)-5-dimethylamino-3-ethyl-1H-pyrazol-4-ylmethyl]-1,2,3,4-tetrahydro-isoquinolin-3yl}-methanol By the general method of Example 4D, and utilizing (+)-3-hydroxymethyl-1,2,3,4-tetrahydroisoquinoline as the nucleophilic reactant and the compound of Example 27C (762 mg, 2.0 mmol) as the substrate, the title compound was prepared and isolated as an amorphous solid (190 mg). TLC R$_f$ (silica gel plates; u.v. detection; ethylacetate/hexane=1.4 in volume): 0.16.

$^{13}$C NMR (CDCl$_3$) 156.5, 151.4, 136.7, 136.6, 133.6, 133.3, 129.0, 127.8, 126.9, 126.5, 126.0, 125.7, 125.6, 124.2, 120.5, 117.0, 107.2, 61.9, 58.2, 47.8, 45.7, 42.6, 26.6, 20.7, 13.2.

EXAMPLE 29

A. 5-Amino-3-ethyl-1-trichlorophenyl)-1H-pyrazole-4-carboxylic acid methyl ester By the general method of Example 27A, 2-cyano-3-ethyl-3-ethoxy-acrylic acid methyl ester (145 g, 0.79 mol) was reacted with 2,4,6-trichlorophenylhydrazine (167 g, 0.79 mol) to afford (following flash chromatography on 40 micron mesh silica gel; elution with ethylacetate/hexane= 1:4 in volume) the title compound as an orange oil (176 g). TLC $R_f$ (silica gel plates, u.v. detection; ethylacetate/ hexane=1:4 in volume): 0.43.

$^1$H NMR (CDCl$_3$): 7.43 (2H, s), 5.14 (2H, broad s), 3.78 (3H, s), 2.74 (2H, q, J=7.6 Hz), 1.20 (3H, t, J=7.6 Hz).

B. 5-Dimethylamino-3-ethyl-1-(2,4,6-trichlorophenyl-1H-pyrazole-4-carboxylic acid methyl ester By the general method of Example 4B, utilizing the Step A compound (4.64 g, 1.3 mmol), the title compound (2.9 g) was prepared and isolated as an orange solid. TLC $R_f$ (silica gel plates; u.v. detection; ethylacetate/hexane=1:10 in volume): 0.42.

$^1$H NMR (CDCl$_3$): 7.44 (2H, s), 3.64 (3H, s), 2.84 (2H, q, J=7.6 Hz), 2.70 (6H, s), 1.23 (3H, t, J=7.6 Hz).

C. [5-Dimethylamino-3-ethyl-1-(2,4,6-trichlorophenyl-1H-pyrazol-4yl]-methanol By the general method of Example 27C and utilizing the Step B compound of this Example (1.50 g, 4.0 mmol), the title compound was prepared and isolated as a colorless waxy solid (320 mg). TLC $R_f$ (silica gel plates; u.v. detection; ethylacetate/hexane=1:4 in volume): 0.16. $^1$H NMR (CDCl$_3$) 7.36 (2H, s), 4.50 (2H, m), 2.65 (6H, s), 2.58 (2H, q, J=7.6 Hz), 1.21 (3H, t, J=7.6 Hz).

D. Enantiomeric {2-[5-Dimethylamino-3-ethyl-1-(2,4,6-trichlorophenyl)-1H-pyrazol-4-ylmethyl]-1,2,3,4-tetrahydroisoquinolin-3-yl}-methanol By the general method of Example 4D and utilizing the dextrorotatory enantiomer (+)-3-hydroxy-1,2,3,4-tetrahydroisoquinoline (240 mg, 1.4 mmol) as the nucleophilic reactant and the in situ formed mesylate of the Step C compound as the substrate, the title compound was prepared and isolated as a light yellow oil [12 mg of pure material following flash chromatography (silica gel; 40 micron mesh; elution with ethylacetate/hexane=1:6 in volume) of the crude product].

$^{13}$C NMR (CDCl$_3$) 155.5, 151.9, 135.3, 134.9, 134.1, 133.5, 128.9, 128.6, 126.7, 126.2, 109.3, 86.8, 71.6, 58.2, 50.6, 43.1, 31.3, 20.5, 13.8. HRMS m/z 493.1345 (M+1, C$_{24}$H$_{28}$N$_4$OCl$_3$).

EXAMPLE 30

[2-(2,6-Dichloro-4-trifluoromethylphenyl)-4-(3-ethoxymethyl-3,4-dihydro-1H-isoquinolin-2-ylmethyl)-5-methylsulfanyl-2H-pyrazol-3-yl)]-dimethylamine, dihydrochloride salt To an ambient temperature solution of the free base form of the title compound of this Example (38 mg) in anhydrous hydrochloric acid/diethyl ether (0.5 ml), 5 drops of a saturated anhydrous hydrochloric acid/diethyl ether solution were added. Immediately, a white crystalline salt (the title compound) formed which was filtered and dried in vacuo (35 mg, m.p. 75.0°–75.3° C.).

EXAMPLE 31

The following compounds were prepared according to the method of the Example listed in Table 1.

TABLE 1

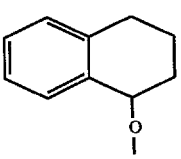

| Z | NMR Data | Method of Example |
|---|---|---|
| Benzyloxy | $^{13}$C NMR (CDCl$_3$): 152.9, 149.9, 138.3, 136.1 135.5; 134.6, 128.7, 128.4, 128.0, 127.6, 108.2, 72.0, 61.9, 42.7, 15.3. | 22 |
| (tetrahydronaphthalenyloxy) | $^{13}$C NMR (CDCl$_3$): 152.7, 149.9, 137.6, 136.9, 136.1, 135.4, 134.7, 129.7, 128.9, 128.7, 127.4, 125.6, 108.7, 74.5, 60.1, 42.8, 29.2, 27.9, 18.9, 15.4. | 22 |
| 3-Hexyloxy | $^1$H NMR (CDCl$_3$): 0.88 (1H, m), 1.08 (8H, m), | 22 |

TABLE 1-continued

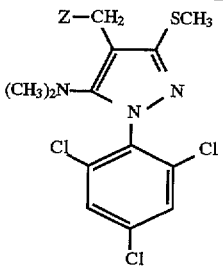

| Z | NMR Data | Method of Example |
|---|---|---|
| | 1.26 (2H, m), 2.48 (3H, s), 2.52 (3H, m), 2.67 (6H, s), 2.69 (2H, m), 3.46 (3H, m), 7.45 (2H, s). | |
| N(C₂H₅)₂ (4-trifluoromethyl rather than 4-chloro) | ¹H NMR (CDCl₃): 1.04 (6H, t), 2.47 (3H, s), 2.52 (4H, q), 2.66 (6H, s) 3.43 (2H, s), 7.68 (2H, s). | 10 |
| Cyclopropylamino | ¹³C NMR (CDCl₃): 151.5, 148.9, 136.2, 135.3, 134.7, 128.6, 110.6, 43.0, 42.2, 30.0, 15.0, 6.5 | 7 |
| Cyclopentylamino | ¹³C NMR (CDCl₃): 151.5, 148.8, 136.2, 135.3, 134.7, 128.6, 110.8, 59.4, 42.9, 41.6, 33.2, 24.1, 15.1 | 7 |
| (3-Methoxyphenyl)-2-aminoethyl | ¹H NMR (CDCl₃): 2.02 (1H, broad s), 2.50 (3H, s), 2.66 (6H, s), 3.72 (2H, s), 3.82 (3H, s), 3.85 (2H, s), 6.80 (1H, m), 6.96 (2H, overlapping multiplets), 7.75 (1H, m), 7.44 (2H, s). | 7 |
| 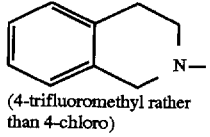 (4-trifluoromethyl rather than 4-chloro) | ¹H NMR (CDCl₃): 2.52 (3H, s), 2.65 (6H, s), 2.76 (2H, m), 2.90 (2H, m), 3.55 (2H, s), 3.68 (2H, s), 7.0–7.19 (4H, m), 7.71 (2H, s). | 10 |
| N(C₂H₅)₂ | ¹³C NMR (CDCl₃): 151.8, 149.7, 136.2, 135.2, 134.8, 128.6, 109.8, 47.1, 46.0, 42.4, 15.1, 11.5. | 7 |
| 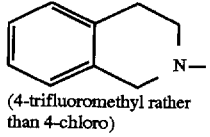 | ¹³C NMR (CDCl₃): 152.3, 149.7, 136.1, 135.3, 135.2, 134.7, 128.6, 126.5, 126.0, 125.5, 108.5, 55.7, 51.4, 49.8, 42.4, 29.5, 15.2. ¹H NMR (CDCl₃): 2.50 (3H, s), 2.64 (6H, s), 2.75 (2H, m), 2.90 (2H, m), 3.54 (2H, s), 3.67 (2H, s), 7.0–7.17 (4H, m), 7.45 (2H, s). | 7 |
| 2-Cyclopropylmethyleneamino | ¹H NMR (CDCl₃): 0.12 (2H, m), 0.46 (2H, m), 0.97 (1H, m), 1.67 (1H, broad s), 2.46 (3H, s), 2.66 (6H, s), 3.68 (2H, s), 7.41 (2H, s). | 7 |
| 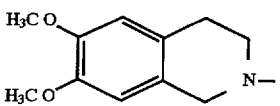 | ¹³C NMR (CDCl₃): 152.3, 149.6, 147.4, 147.1, 136.1, 135.3, 134.7, 128.6, 127.0, 126.5, 111.4, 109.5, 108.5, 55.9, 55.9, 55.3, 53.5, 51.4, 50.0, 42.4, 29.1, 15.1. | 7 |

TABLE 1-continued

[Structure: pyrazole ring with Z—CH2 and SCH3 substituents, (CH3)2N group, and N-linked 2,4,6-trichlorophenyl group]

| Z | NMR Data | Method of Example |
|---|---|---|
| [1,2,3,4-tetrahydroquinolin-1-yl] | ¹H NMR (CDCl₃): 1.9 (2H, m), 2.40 (3H, s), 2.46 (6H, s), 2.66 (2H, t), 3.22 (2H, t), 3.70 (2H, s), 6.4 (1H, m), 6.6–6.8 (3H, m), 7.17 (1H, s), 7.36 (1H, s). | 7 |
| [1,2,3,4-tetrahydronaphthalen-1-ylamino] | ¹³C NMR (CDCl₃): 151.7, 149.1, 139.3, 137.5, 136.2, 135.4, 134.8, 129.2, 129.0, 128.6, 126.7, 125.8, 110.7, 55.3, 43.0, 40.7, 29.5, 28.0, 18.9, 15.2. | 7 |
| [2,6-dimethylpiperidin-1-yl] | ¹³C NMR (CDCl₃): 157.7, 149.5, 136.4, 135.2, 135.0, 128.6, 111.7, 54.3, 45.1, 42.4, 32.6, 18.9, 18.8, 15.1. | 7 |
| (p-chlorobenzyl)-(3-propanol)amino | ¹³C NMR (CDCl₃): 151.8, 149.9, 137.1, 136.2, 135.6, 135.0, 133.0, 131.0, 128.7, 128.4, 107.5, 63.1. 58.2, 52.6, 48.1, 42.3, 28.6, 14.7. | 7 |
| (m-chlorobenzyl)-(3-propanol)amino | ¹³C NMR (CDCl₃): 151.8, 149.9, 140.9, 136.2, 135.5, 134.8, 134.1, 129.6, 129.5, 128.7, 127.6, 127.3, 107.6, 62.9, 58.3, 52.4, 48.1, 42.3, 28.8, 14.7. | 7 |
| (m-methoxybenzyl)-(3-propanol)amino | ¹³C NMR (CDCl₃): 159.6, 151.8, 150.0, 140.3, 136.2, 135.5, 134.9, 129.2, 128.6, 121.9. 114.8, 113.0, 107.8, 63.0, 59.0, 55.2, 52.5, 48.1, 42.3, 28.7, 14.7. | 7 |
| (p-methylbenzyl)-(3-propanol)amino | ¹³C NMR (CDCl₃): 151.8, 150.1, 136.8, 136.2, 136.1, 135.5, 135.3, 134.9, 129.7, 128.9, 128.6, 107.7, 63.3, 58.7, 52.6, 48.1, 42.2, 28.6, 21.1, 14.7. | 7 |
| (p-nitrobenzyl)-(3-propanol)amino | ¹³C NMR (CDCl₃): 151.8, 149.7, 147.1, 147.07, 136.1, 135.6, 134.7, 130.0, 129.8. 128.7, 123.5, 107.6, 62.4, 58.2, 52.4, 48.4, 42.5, 29.0, 14.5. | 7 |
| [octahydroindol-1-yl] | ¹³C NMR (CDCl₃): 151.6, 149.2, 136.3, 136.2, 135.3, 128.6, 110.8, 63.7, 51.6, 47.1, 42.5, 38.4, 29.8, 28.6, 25.7, 24.9, 21.4, 15.1. | 7 |
| benzylmethylamino | ¹³C NMR (CDCl₃): | 7 |

TABLE 1-continued

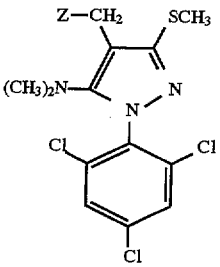

| Z | NMR Data | Method of Example |
|---|---|---|
| benzyl(2-hydroxyethyl)amino | 152.0, 149.9, 139.5, 136.2, 135.3, 134.8, 129.2, 128.6, 128.2, 126.9, 109.1, 62.2, 51.3, 42.6, 41.3, 15.0. $^{13}$C NMR (CDCl$_3$): 151.7, 149.4, 138.8, 136.2, 135.5, 134.8, 129.5, 129.0, 128.6, 128.3, 128.2, 127.2, 108.7, 59.0, 58.9, 55.0, 47.9, 42.9, 14.5. | 7 |
| 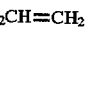 | $^{13}$C NMR (CDCl$_3$): 152.0, 149.7, 136.1, 135.3, 134.9, 134.8, 134.6, 133.9, 129.1, 128.6, 126.5, 126.1, 125.5, 116.7 (2), 109.2, 72.2, 69.4, 56.2, 50.4, 47.8, 42.4, 30.8, 15.2. | 13 |

EXAMPLE 32

The following compounds were prepared according to the coupling method of Example 4D, followed by the alkylation according to the method of Example 15 for those compounds of Table 2 wherein R" is not hydrogen, and they were derived from the dextrorotary enantiomer (+)-3-substituted-1,2,3,4-tetrahydroisoquinoline prepared by the general method of Preparation 2 hereafter. The pyrazole starting material was prepared by the method of the Example listed in Table 2.

TABLE 2

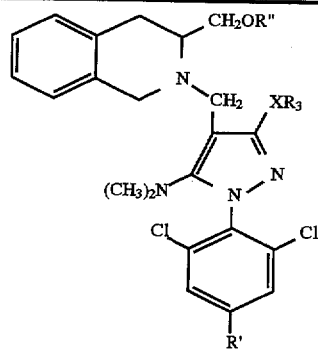

| R' | R" | XR$_3$ | NMR or HRMS | Method of Example |
|---|---|---|---|---|
| CF$_3$ | CH$_3$ | C$_2$H$_5$ | HRMS m/z 541.1710 (M + 1, C$_{26}$H$_{30}$N$_4$OCl$_2$F$_3$ | 27C |
| Cl | CH$_3$ | C$_2$H$_5$ | $^{13}$C NMR (δ, CDCl$_3$) ppm 156.1, 151.6, 136.2, 135.0, 134.6, 133.9, 129.1, 128.5 (2), 126.5, 126.1, 125.6, 107.5, 72.3, 58.9, 56.3, 50.3, 47.1, 42.6, 30.4, 20.7, 13.5. | 29C |
| CF$_3$ | C$_2$H$_5$ | C$_2$H$_5$ | HRMS m/z 554.1853 (M, C$_{27}$H$_{31}$N$_4$OCl$_2$F$_3$) | 27C |
| Cl | H | C$_3$H$_7$ | $^{13}$C NMR (δ, CDCl$_3$) ppm 154.8 151.5, 136.4, 135.4, 133.6, 133.2, 129.0, 128.6, 127.0, 126.5, 126.1, 107.5, 62.1, 58.0, 47.5, 45.5, 42.6, 29.3, 26.0, 22.2, 13.7. | 29C |

EXAMPLE 33

The following compounds were prepared according to the methods of the Examples listed in Table 3.

TABLE 3

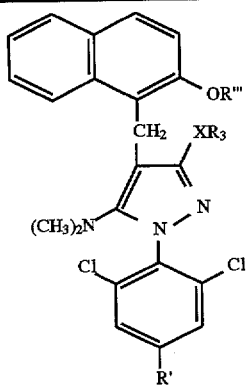

| R' | R''' | XR₃ | NMR or HRMS | Method of Example |
|---|---|---|---|---|
| Cl | CH₂—△ | SCH₃ | HRMS m/z 545.08672 (M, $C_{27}H_{26}Cl_3N_3OS$) | 21, 23 |
| Cl | C₂H₅ | OCH₃ | ¹³C NMR (δ, CDCl₃) ppm 162.5, 153.9, 150.2, 136.9, 135.2, 134.9, 133.5, 129.4, 128.4, 128.2, 127.9, 125.7, 124.4, 123.1, 122.5, 114.8, 98.9, 65.0, 55.4, 41.6, 17.8, 15.2. | 5D, 21, 23 |
| Cl | CH₂CH=CH₂ | SCH₃ | ¹³C NMR (δ, CDCl₃) ppm 153.9, 149.9, 148.4, 136.3, 135.3, 135.2, 133.9, 133.6, 129.5, 128.5, 128.3, 125.9, 124.4, 123.4, 121.7, 117.3, 114.8, 112.7, 70.4, 41.7, 19.9, 15.2. | 21, 23 |
| Cl | C₂H₅ | SCH₃ | ¹³C NMR (δ, CDCl₃) ppm 154.2, 149.9, 148.4, 136.3, 135.2, 135.1, 133.6, 129.3, 128.4, 128.2, 125.8, 124.4, 123.2, 121.4, 114.5, 112.8, 64.9, 41.6, 19.9, 15.3, 15.2. | 21, 23 |
| Cl | CH(CH₃)₂ | SCH₃ | ¹³C NMR (δ, CDCl₃) ppm 154.2, 149.9, 148.4, 136.3, 135.2, 135.1, 133.7, 129.3, 128.4, 128.2, 125.8, 124.4, 123.1, 121.2, 114.3, 112.8, 75.7, 41.5, 28.8, 19.8, 19.5, 15.2. | 21, 23 |
| Cl | H | C₂H₅ | HRMS m/z 473.0651 (M, $C_{24}H_{22}Cl_3N_3O$) | 29C, 21 |
| Cl | C₂H₅ | C₂H₅ | ¹³C NMR (δ, CDCl₃) ppm 155.0, 154.0, 149.2, 136.5, 136.0, 135.1, 133.6, 129.3, 128.4, 128.3, 128.1, 125.8, 124.2, 123.2, 121.5, 114.2, 110.6, 64.7, 42.1, 20.9, 19.5, 15.3, 13.0. | 29C, 21, 23 |
| Cl | H (6-methoxy substituted) | SCH₃ | ¹³C NMR (δ, CDCl₃) ppm 155.6, 151.2, 149.0, 148.1, 136.5, 136.4, 135.2, 130.4, 128.8, 128.5, 127.2, 125.3, 120.0, 118.7, 118.4, 113.1, 106.9, 55.3, 42.7, 19.8, 16.0. | 21 |
| CF₃ | H | C₂H₅ | HRMS m/z 508.12123 (M + 1, $C_{25}H_{23}N_3OCl_2F_3$) | 27C, 21 |
| CF₃ | C₂H₅ | C₂H₅ | HRMS m/z 536.15083 (M + 1, $C_{27}H_{27}N_3OCl_2F_3$) | 27C, 21, 23 |

EXAMPLE 34

The following compounds were prepared according to the method of Example 23. The starting compounds of use in this method were prepared by the method of Example 21.

TABLE 4

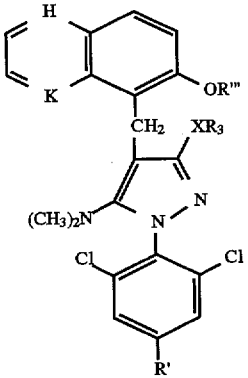

| R' | R''' | XR₃ | H | K | NMR (CDCl₃) ppm |
|---|---|---|---|---|---|
| Cl | CH₃ | SCH₃ | N | CH | ¹³C NMR: 154.9, 150.0, 148.1, 147.4, 143.7, 142.2, 136.2, 135.5, 135.0, 133.1, 129.3, 128.5, 121.1, 120.6, 116.8, 112.0, 56.5, 41.6, 19.5, 15.1. |
| CF₃ | CH₃ | C₂H₅ | CH | N | ¹H NMR: 8.96 (1H, m), 8.19 (1H, m), 7.79 (1H, m), 7.66 (2H, s), 7.3–7.42 (2H, two overlapping multiplets), 4.63 (3H, s), 3.87 (6H, s), 2.24 (2H, q, J=7.5 Hz), 0.92 (3H, t, J=7.5 HZ) |
| Cl | CH₃ | SCH₃ | CH | N | ¹³C NMR: 158.4, 150.0, |

TABLE 4-continued

[Structure: pyrazole core with CH2 linker to aromatic ring bearing H, K positions and OR''' group; (CH3)2N substituent; N-aryl with 2,6-dichloro and 4-R' substituents; XR3 substituent]

| R' | R''' | XR₃ | H | K | NMR (CDCl₃) ppm |
|---|---|---|---|---|---|
| CF₃ | C₂H₅ | C₂H₅ | CH | N | 149.6, 148.9, 147.6, 146.0, 136.3, 135.1, 128.4, 127.3, 124.0, 123.5, 118.7, 114.4, 113.4, 56.3, 42.4, 18.9, 15.5. ¹³C NMR: 155.8, 149.4, 149.0, 140.0, 136.8, 132.6, 132.0, 128.0, 127.4, 125.5, 125.4, 124.3, 123.5, 120.8, 118.4, 115.2, 111.0, 64.6, 42.5, 21.0, 18.9, 14.9, 12.9. |

EXAMPLE 35

A. 2-{1-[1-(2,6-Dichloro-4-trifluoromethylphenyl)-5-dimethylamino-3-ethyl-1H-pyrazol-4-ylmethyl]-napthalen-2-yloxy}-ethanol tert-butyl-dimethylsilyl ether

To a well-stirred solution of 1-[1-(2,6-Dichloro-4-trifluoromethylphenyl)-5-dimethylamino-3-ethyl-1H-pyrazol-4-ylmethyl]-napthalen-2-ol (130 mg, 0.26 mmol) (listed in Table 3) in tetrahydrofuran (1.0 ml), sodium hydride (31 mg of 60% sodium hydride mineral oil dispersion; 19 mg, 0.78 mmol of sodium hydride) was added portionwise over five minutes; and five minutes thereafter 744 mg (2.6 mmol) of 1-iodo-2-(tert-butyldimethylsilyloxy)ethane was added before heating the mixture for 18 hours at 45°–50° C. TLC examination showed incomplete reaction. Twice more, 744 mg (2.6 mmol) additions of 1-iodo-2-(tert-butyldimethylsilyloxy)ethane were made, each time followed by heating the reaction at 50° C. for 18 hours. After removing solvent in vacuo, the residue was extracted with ethyl acetate/water (100 ml of each). The separated organic extract was dried (anhydrous sodium sulfate) and concentrated in vacuo to an oil. Flash chromatography (silica gel, 40 micron mesh; elution with ethyl acetate/hexane 5:95 in volume) afforded the title compound as an oil (53 mg). ¹H NMR (CDCl₃): 0.07 (6H, s), 0.88 (9H, s), 0.92 (3H, t, J=7.5 Hz), 2.24 (2H, q, J=7.5 Hz), 2.42 (6H, s), 3.96 (2H, t), 4.15 (2H, t), 7.16–7.32 (3H, m), 7.58 (2H, s), 7.64–7.75 (2H, m), 7.8–7.88 (1H, m).

B. 2-{1-[1-(2,6-Dichloro-4-trifluoromethylphenyl)-5-dimethylamino-3-ethyl-1H-pyrazol-4-ylmethyl]-napthalen-2-yloxy}-ethanol

A solution of the compound of step A (50 mg, 0.075 mmol) and tetrabutylammonium fluoride (150 μl of a 1.00M tetrahydrofurane solution, 0.15 mol) in tetrahydrofuran (0.25 ml) was stirred at ambient temperature for 2 hours. The entire sample was dissolved in ethyl acetate/water (50 ml of each). The separated organic extract was then extracted twice with equal volumes of water, dried (anhydrous sodium sulfate), and concentrated in vacuo to an oil (50 mg). Flash chromatography of the entire sample (silica gel, 40 micron mesh; elution with ethyl acetate/hexane =3:7 in volume) afforded the title compound (27 mg) as an amorphous solid.

TLC R_f (silica gel plates, u.v. detection, ethyl acetate/water=3:7 in volume): 0.34; ¹H NMR (CDCl₃): 1.00 (3H, t, J=7.5 Hz), 2.12 (1H, broad m), 2.34 (2H, q, J=7.5 Hz), 2.47 (6H, s), 3.95–4.08 (2H, m), 4.24 (2H, t), 4.33 (2H, s), 7.25–7.46 (3H, m), 7.68 (2H, s), 7.75–7.94 (2H, m), 8.00 (1H, m).

EXAMPLE 36

2-{8-[1-(2,6-Dichloro-4-trifluoromethyl-phenyl)-5-dimethylamino-3-ethyl-1H-pyrazol-4-ylmethyl]-quinolin-7-yloxy}-ethanol

By the method of Example 35, the compound of Example 27D (200 mg, 0.39 mmol) was converted into the title compound (36 mg, isolated as an amorphous solid). ¹HNMR (CDCl₃): 0.96 (3H, t), 2.02 (1H, broad), 2.34 (6H, s), 3.86 (2H, m), 4.13 (2H, t), 4.61 (2H, s), 7.14–7.42 (2H, overlapping multiplets), 7.61 (2H, s), 7.71 (1H, d), 8.08 (1H, dd), 8.88 (1H, m).

The following Preparations illustrate the preparation of intermediates.

Preparation 1

Racemic (1,2,3,4-Tetrahydro-isoquinolin-3-yl)-methanol [also referred to as(±)-3-hydroxymethyl-1,2,3,4-tetrahydroisoquinoline]

To a well stirred, ice-bath-chilled slurry of 1,2,3,4-tetrahydroisoquinoline-3-carboxylic acid hydrochloride (75 g, 0.351 mol. Aldrich Chemical Co.) in anhydrous methanol (600 ml), sodium methoxide (37.92 g, 0.702 mol) was added in small solid portions over a 10 minute period. After 30 minutes of brisk stirring, the methanol was removed and the colorless residue was dried in vacuo overnight. The entire sample was stirred in anhydrous tetrahydrofuran causing the organic portion to dissolve completely. A 1.0M solution of lithium aluminum hydride in tetrahydrofuran (351 ml, 0.351 mol) was added in a rapid stream to the well-stirred mixture over a 20 minute period (mild exotherm). The reaction mixture was then vigorously refluxed for 2 hours. At 5° C., the reaction was quenched by cautious addition of 15% aqueous sodium hydroxide. The mixture was filtered, and the filtrate was concentrated in vacuo to a yellow solid. The entire sample was then dissolved in methylene chloride (400 ml) and filtered to remove residual inorganic salts. Solvent removal in vacuo afforded the title compound as an orange solid (47.01 g, 70% yield). TLC R_f (silica gel plates, u.v. detection, methanol/methylene chloride=5:95 in volume): 0.46; ¹³C NMR (CDCl₃): 135.4, 134.1, 129.3, 126.3, 126.1, 125.9, 65.4, 55.0, 47.8, 30.9.

Preparation 2

Dextrorotatory enantiomer of (1,2,3,4-Tetrahydro-isoquinolin-3-yl)-methanol (also referred to as (+)-3-hydroxymethyl-1,2,3,4-tetrahydroisoquinoline)

To a solution of (+)-3-hydroxymethyl-1,2,3,4-tetrahydroisoquinoline (Preparation 1; 47.01 g, 0.288 mol)

in isopropyl alcohol (159 ml), a solution of (S)-(+)-mandelic acid –(43.81 g, 0.288 mol) in isopropyl alcohol (159 ml) was added. The resulting solution was allowed to stand at ambient temperature for 48 hours, during which time a heavy orange crystalline mass formed. The isolated crystalline solid (13.06 g) was dissolved in hot isopropyl alcohol (63 ml). After standing for 1 hour at ambient temperature, the newly-formed crystalline solid was isolated by filtration (8.2 g, m.p. 138° C.). The recrystallization procedure was repeated twice more, using 63 ml and 60 ml volumes of isopropyl alcohol to afford 7.08 g and 6.76 g of crystalline material, respectively. (In each case, the crystallization was allowed to proceed for 2 hours at ambient temperature prior to filtration.) A 138°–139° C. m.p. was observed after the final crystallization. The entire sample was dissolved in methylene chloride water (300 ml and 100 ml, respectively) with the pH adjusted to 9.5 (potassium carbonate). The phases were separated, and the aqueous portion was extracted with three 50 ml portions of fresh methylene chloride. The combined organic extracts were dried (anhydrous sodium sulfate) and concentrated in vacuo to afford the optically resolved title compound as a colorless amorphous solid (2.02 g, 8.6% yield). $[\alpha]^{20}_D +103°$ (c=1.83, $CH_2Cl_2$); $^{13}C$ NMR ($CDCl_3$): identical to that of the racemic compound prepared in Preparation 1.

Preparation 3

Levorotatory enantiomer of (1,2,3,4-Tetrahydro-isoquinolin-3-yl)-methanol [also referred to as (–)-3-hydroxymethyl-1,2,3,4-tetrahydroisoquinoline]

Substituting (R)-(–)-mandelic acid for (S)-(+)-mandelic acid in the Preparation 2 procedure (and utilizing 17.9 g of the alcohol-amine prepared in Preparation 1), the levorotatory title compound (0.65 g, 7.3% yield) was obtained as a colorless amorphous solid. $[\alpha]^{20}_D -100.4°$ ($CH_2Cl_2$, c=1.43); $^1H$ NMR and $^{13}C$ NMR ($CDCl_3$): identical in all respects to those observed for the racemic (Preparation 1) and dextrorotatory (Preparation 2) products.

I claim:
1. A compound of the formula

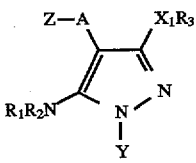

or a pharmaceutically acceptable acid addition salt thereof, wherein
A is $CH_2$;
$X_1$ is a covalent bond, $CH_2$, NR, wherein R is hydrogen, linear $C_1$–$C_6$ alkyl or branched $C_3$–$C_8$ alkyl, O, or S;
$R_1$, $R_2$ and $R_3$ are each independently linear $C_1$–$C_6$ alkyl, branched $C_3$–$C_8$ alkyl, $C_3$–$C_8$ alkenyl wherein the double bond is not adjacent to the N or $X_1$ when $X_1$ is oxygen or sulfur, or $C_3$–$C_7$ cycloalkyl $(CH_2)_n$ wherein n is 0, 1, 2, 3 or 4; or $R_1$ and $R_2$ when taken together with the nitrogen form a saturated four, five or six membered ring optionally condensed with benzo; and $R_3$ may also be $(CH_2)_q Q_1 R_{19}$ wherein q is 0, 1 or 2, $Q_1$ is O, S, NH, N($C_1$–$C_6$ alkyl) or a covalent bond when X is not a covalent bond, and $R_{19}$ is hydrogen, linear $C_1$–$C_6$ alkyl, branched $C_3$–$C_8$ alkyl, $C_3$–$C_8$ alkenyl, or $C_3$–$C_6$ cycloalkyl $(CH_2)_n$ wherein n is 0 to 4;

Y is phenyl, thienyl, benzothienyl, pyridyl, quinolyl, pyrazinolyl, pyrimidyl, imidazolyl, benzimidazolyl, furanyl, benzofuranyl, thiazolyl, benzothiazolyl, isothiazolyl, benzisothiazolyl, isoxazolyl, benzisoxazolyl, triazolyl, pyrazolyl, pyrrolyl, indolyl, azaindolyl, oxazolyl, benzoxazolyl, pyrrolidinyl, thiazolidinyl, morpholinyl, or piperidinyl, each of which may be substituted by one to three of any one of fluoro, chloro, bromo, or methyl, or one of trifluoromethyl; with the proviso that Y is not unsubstituted phenyl; and
Z is
(a)

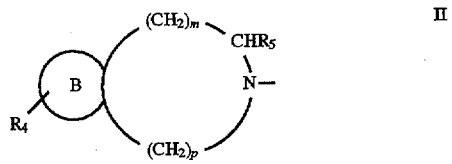

wherein the B ring is phenyl, naphthyl, pyridyl, pyrimidinyl, pyrazinyl, pyridazinyl, triazilyl, pyrrolyl, pyrazolyl, imidazolyl, triazolyl, thienyl, or indolyl, each of which may be substituted by methyl, methoxy, fluoro, chloro, bromo or iodo; or a saturated 5- or 6-membered carbocyclic ring or a partially unsaturated ring having one or two double bonds;
$R_4$ is hydrogen, $C_1$–$C_6$ alkyl, $C_1$–$C_6$ alkoxy, or hydroxy, fluoro, chloro, bromo, iodo, or trifluoromethyl;
$R_5$ is hydrogen, linear $C_1$–$C_6$ alkyl, branched $C_3$–$C_8$ alkyl, $C_3$–$C_8$ alkenyl, or $(CH_2)_o$—$X_2$—$(CH_2)_r$—$Q_2$—$R_6$;
$R_6$ is hydrogen, linear $C_1$–$C_6$ alkyl, branched $C_3$–$C_8$ alkyl, or $C_3$–$C_8$ alkenyl;
$X_2$ and $Q_2$ are each independently O, S, NH, N($C_1$–$C_6$ alkyl), or one of $X_2$ and Q may be a covalent bond;
m is 0 or 1;
o is 1 or 2;
p is 1 or 2;
r is 0, 1, or 2;
(b)

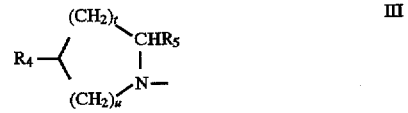

wherein $R_4$ and $R_5$ are as defined above, and t and u are each independently 1 or 2;
(c) —$NR_7R_8$ wherein $R_7$ and $R_8$ are each independently hydrogen, $C_1$–$C_6$ linear alkyl, branched $C_3$–$C_8$ alkyl, $C_3$–$C_8$ alkenyl, $(CH_2)_v CH_2OH$, $(CH_2)_v NR_9 R_{10}$, wherein v is 0 to 3, and $R_9$ and $R_{10}$ are each independently hydrogen, or linear $C_1$–$C_6$ alkyl; $C_1$–$C_{12}$ cycloalkyl, ($C_3$–$C_{12}$ cycloalkyl) $(CH_2)_n$, ($C_6$–$C_{10}$ bicycloalkyl) $(CH_2)_n$, wherein n is 0 to 4, benzofused $C_3$–$C_6$ cycloalkyl, $C_1$–$C_6$ hydroxyalkyl, phenyl, phenyl ($C_1$–$C_3$ alkylene), each of which may be substituted by one or two of hydroxy, fluoro, chloro, bromo, $C_1$–$C_5$ alkyl, or $C_1$–$C_5$ alkoxy; or $R_7$ and $R_8$ may be taken together with the nitrogen to form a saturated or partially unsaturated 5- to 7-membered ring which may contain one of O, S, NH or N($C_1$–$C_6$ alkyl) and which may be substituted by $C_1$–$C_6$ alkyl, hydroxy or phenyl wherein any double bond(s) are not adjacent to any heteroatoms;

(d)

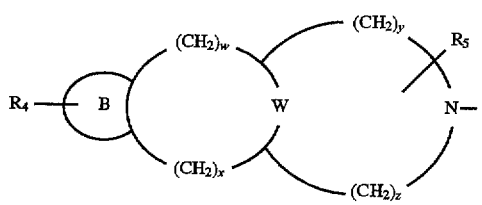

wherein B, $R_4$ and $R_5$ are as defined above, w, x, y and z are each independently 1 or 2, and W is $(CH_2)_q$ wherein q is as defined above, $N(C_1-C_6$ alkyl), or oxygen;

(e)

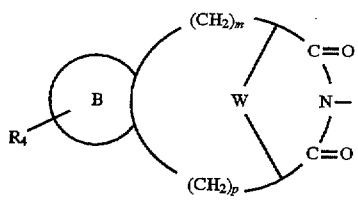

wherein B, $R_4$, m and p are as defined above;

(f)

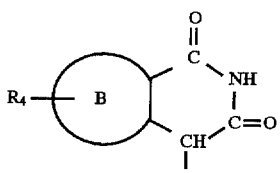

wherein B and $R_4$ are as defined above;

(g) $O(CH_2)_v R_{11}$
wherein v is 0 to 3 and $R_{11}$ is linear $C_1-C_6$ alkyl, branched $C_3-C_8$ alkyl, phenyl, naphthyl, 1,2,3,4-tetrahydronaphthyl, thienyl, benzothienyl, pyridyl, quinolyl, pyrazinolyl, pyrimidyl, imidazolyl, benzimidazolyl, furanyl, benzofuranyl, thiazolyl, benzothiazolyl, isothiazolyl, benzisothiazolyl, isoxazolyl, benzisoxazolyl, triazolyl, pyrazolyl, pyrrolyl, indolyl, azaindolyl, oxazolyl, benzoxazolyl, pyrrolidinyl, thiazolidinyl, morpholinyl, piperidinyl, or thienyl, each of which may be substituted by one or two of any one of fluoro, chloro, bromo, methyl, or trifluoromethyl;

(h)

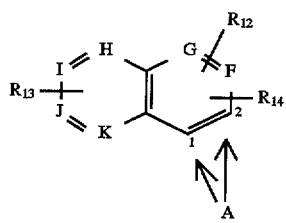

wherein A is defined above and is linked to position 1 or 2 while $R_{14}$ is attached to position 2 or 1, respectively; F, G, H, I, J and K are independently C or N, provided that not more than three of H, I, J and K are N with not more than two adjacent nitrogens; $R_{12}$ and $R_{13}$ each independently are hydrogen, linear $C_1-C_6$ alkyl, branched $C_3-C_8$ alkyl, $C_3-C_8$ alkenyl, fluoro, chloro, bromo, trifluoromethyl, hydroxy, thiol, $C_1-C_{12}$ alkoxy, $C_1-C_{12}$ thioalkanyl, $C_3-C_{12}$ alkenoxy or $C_3-C_{12}$ thioalkenyl wherein the double bond is not adjacent to the oxygen or sulfur, and $R_{14}$ is hydroxy, $C_1-C_{12}$ alkoxy, $C_3-C_{12}$ alkenoxy wherein the double bond is not adjacent to the oxygen, or $-X_2-(CH_2)_rQ_2R_6$ wherein $X_2$, r, $Q_2$ and $R_6$ are as defined above in paragraph (a) except that $Q_2$ is not sulfur, or $R_{14}$ is $NR_{15}R_{16}$ wherein $R_{15}$ and $R_{16}$ are each independently hydrogen, linear $C_1-C_6$ alkyl, branched $C_3-C_8$ alkyl, $C_3-C_8$ alkenyl wherein the double bond is not adjacent to the nitrogen, or $C_3-C_7$ cycloalkyl-$(CH_2)_n$ wherein n is as defined above, or $R_{15}$ and $R_{16}$ together with the nitrogen form a saturated five or six membered ring optionally condensed with benzo; or (i)

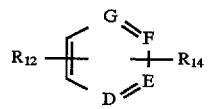

wherein D,E,F and G are independently C or N, provided that not more than two of D,E,F and G are N, and $R_{12}$ and $R_{14}$ are as defined in paragraph (h), A, defined above, is linked to a carbon in formula XV; and $R_{14}$ is linked to a carbon located adjacent to the carbon to which A is linked.

2. A compound according to claim 1 wherein Y is 2,4,6-tri-substituted phenyl.

3. A compound according to claim 2 wherein Y is 2,4,6-trichlorophenyl, 2,6-dichloro-4-trifluoromethylphenyl or 2,6-dibromo-4-fluorophenyl.

4. A compound according to claim 1 wherein $X_1-R_3$ is ethyl or methylthio.

5. A compound according to claim 1 wherein $R_1$ and $R_2$ are each methyl.

6. A compound according to claim 1 wherein Z is $NR_7R_8$ wherein $R_7$ is phenyl or phenyl substituted by one of fluoro, chloro, nitro, methyl or methoxy.

7. A compound according to claim 6 wherein $R_8$ is $CH_2CH_2CH_2OH$, $CH_2CH_2OH$, or methyl.

8. A compound according to claim 1 wherein Z is 1,2,3,4-tetrahydroisoquinolin-2-yl and $R_5$ is $(CH_2)_o-X_2-(CH_2)_r-Q_2-R_6$.

9. A compound according to claim 8 wherein $R_5$ is $(CH_2)_kOH$ wherein k is 1 to 4, or $CH_2OCH_2CH_2OR_6$.

10. A compound according to claim 1 wherein Z is 1, 2, 3, 4-tetrahydroisoquinolin-2-yl, wherein $R_5$ is substituted at position 3, and the absolute configuration at the 3-position is S or R or R,S.

11. A compound according to claim 1 wherein Z is as defined in (h).

12. A compound according to claim 11 wherein A is linked to position 1, $R_{14}$ is at position 2 and is $-X_2-(CH_2)_rQ_2R_6$.

13. A compound according to claim 12 wherein F, G, H, I, and J, are each carbon, K is carbon or nitrogen, and $R_{14}$ is 2-methoxy, 2-ethoxy, 2-isopropoxy, or 2-cyclopropylmethoxy.

14. A compound according to claim 1 wherein Z is

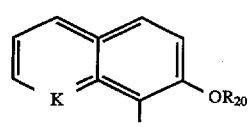

wherein K is C or N and $R_{20}$ is methyl, ethyl, isopropyl, cyclopropylmethylene, or hydroxyethylene.

15. A compound according to claim 1 wherein Z is as defined in (a), B is phenyl, p and m are each 1, and $R_5$ is $CH_2OCH_3$.

16. A compound according to claim 1 wherein Z is

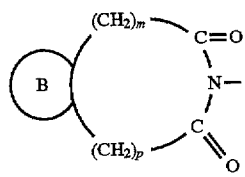

wherein B is phenyl, m is 0, and p is 1.

17. A compound according to claim 1 wherein said compound is

2-{1-[1-(2,6-dichloro-4-trifluoromethylphenyl)-5-dimethylamino-3-ethyl-1H-pyrazol-4-ylmethyl]-napthalen-2-yloxy}-ethanol;

enantiomeric [4-(3-methoxymethyl-3,4-dihydro-1H-isoquinolin-2-ylmethyl)-5-methylsulfanyl-2-(2,4,6-trichlorophenyl)-2H-pyrazol-3-yl]-dimethylamine;

enantiomeric [2-(2,6-dichloro-4-trifluoromethylphenyl)-4-(3-ethoxymethyl-3,4-dihydro-1H-isoquinolin-2-ylmethyl)-5-ethyl-2H-pyrazol-3-yl]-dimethylamine;

[2-(2,6-dichloro-4-trifluoromethylphenyl)-5-ethyl-4-(7-methoxyquinolin-8-ylmethyl)-2H-pyrazol-3-yl]dimethylamine;

[2-(2,6-dichloro-4-trifluoromethylphenyl)-4-)2-ethoxy-napthalen-1-ylmethyl)-5-ethyl-2H-pyrazol-3-yl]-dimethylamine;

[4-(2-ethoxynapthalen-1-ylmethyl)-5-ethyl-2-(2,4,6-trichlrophenyl)-2H-pyrazol-3-yl]-dimethylamine;

[4-(7-methoxyquinolin-8-ylmethyl)-5-methylsulfanyl-2-(2,4,6-trichlorophenyl)-2H-pyrazol-3-yl]-dimethylamine;

2-{1-[5-dimethylamino-3-methylsulfanyl-1-(2,4,6-trichlorophenyl)-1H-pyrazol-4-ylmethyl]-napthalen-2-yloxy}-ethanol;

enantiomeric [2-(2,6-dichloro-4-trifluoromethlphenyl)-5-ethyl-4-(3-methoxymethyl-3,4-dihydro-1H-isoquinolin-2-ylmethyl)-2H-pyrazol-3-yl]-dimethylamine;

[4-(2-cyclopropylmethoxynapthalen-1-ylmethyl)-5-methylsulfanyl-2-(2,4,6-trichlorophenyl)-2H-pyrazol-3-yl]-dimethylamine.

18. A composition for the treatment of (a) illnesses induced or facilitated by corticotropin releasing factor or (b) inflammatory disorders, stress and anxiety related disorders, including stress-induced depression and headache, abdominal bowel syndrome, immune suppression, HIV infections, Alzheimer's disease, gastrointestinal diseases, anorexia nervosa, hemorrhagic stress, drug and alcohol withdrawal symtoms, drug addiction, and fertility problems, which comprises a compound of the formula I as defined in claim 1 and a pharmaceutically acceptable carrier.

19. A compound of the formula

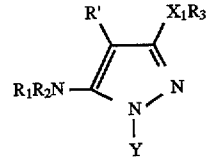

wherein R' is $CH_2OH$ or $C(O)O(C_1-C_3$ alkyl), $R_1$, $R_2$ and $R_3$ are each independently linear $C_1-C_6$ alkyl, branched $C_3-C_8$ alkyl, $C_3-C_8$ alkenyl wherein the double bond is not adjacent to the N or $X_1$ when $X_1$ is oxygen or sulfur, $C_3-C_7$ cycloalkyl $(CH_2)_n$ wherein n is 0, 1, 2, 3 or 4; or $R_1$ and $R_2$ when taken together with the nitrogen form a saturated four, five or six membered ring optionally condensed with benzo;

$X_1$ is a covalent bond, $CH_2NR$, wherein R is hydrogen or linear $C_1-C_6$ alkyl, O, or S; and Y is phenyl, thienyl, benzothienyl, pyridyl, quinolyl, pyrazinolyl, pyrimidyl, imidazolyl, benzimidazolyl, furanyl, benzofuranyl, thiazolyl, benzothiazolyl, isothiazolyl, benzisothiazolyl, isoxazolyl, benzisoxazolyl, triazolyl, pyrazolyl, pyrrolyl, indolyl, azaindolyl, oxazolyl, benzoxazolyl, pyrrolidinyl, thiazolidnyl, morpholinyl, or piperidinyl, each of which may be substituted by one to three of any one of fluoro, chloro, bromo, or methyl, or one of trifluoromethyl; with the proviso that Y is not unsubstituted phenyl.

20. A method for the treatment of stress and anxiety related disorders, including stress-induced depression and headache, abdominal bowel syndrome, inflammatory disorders, immune suppression, HIV infections, Alzheimer's disease, gastrointestinal diseases, anorexia nervosa, hemorrhagic stress, drug and alcohol withdrawal symtoms, drug addiction, and fertility problems, particularly depression, which comprises administering to a subject in need of such treatment a compound of formula I as defined in claim 1 or a pharmaceutically acceptable salt thereof.

21. A method for the treatment of illnesses induced or facilitated by corticotropin releasing factor which comprises administering to a subject in need of such treatment a compound of formula I as defined in claim 1 or a pharmaceutically acceptable salt thereof.

* * * * *